(12) United States Patent
Murrish et al.

(10) Patent No.: US 10,431,336 B1
(45) Date of Patent: Oct. 1, 2019

(54) COMPUTERIZED SYSTEMS AND METHODS FOR FACILITATING CLINICAL DECISION MAKING

(75) Inventors: John Christopher Murrish, Overland Park, KS (US); Douglas S. McNair, Leawood, KS (US); Kanakasabha Kailasam, Olathe, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 13/250,072

(22) Filed: Sep. 30, 2011

Related U.S. Application Data

(60) Provisional application No. 61/389,053, filed on Oct. 1, 2010.

(51) Int. Cl.
*G16H 50/20* (2018.01)

(52) U.S. Cl.
CPC .................................. *G16H 50/20* (2018.01)

(58) Field of Classification Search
CPC ................... G06Q 50/22; G06Q 50/24; G06F 19/322–327; G06F 19/3481;
(Continued)

(56) References Cited

U.S. PATENT DOCUMENTS

| | | |
|---|---|---|
| 4,839,853 A | 6/1989 | Deerwester et al. |
| 5,243,565 A | 9/1993 | Yamamoto |

(Continued)

FOREIGN PATENT DOCUMENTS

| | | |
|---|---|---|
| EP | 1043666 A2 | 10/2000 |
| EP | 2365456 A2 | 9/2011 |

(Continued)

OTHER PUBLICATIONS

Nealon, et al.: Agent-Based Applications in Health Care, Department of Computing, Oxford Brookes University and Computer Science and Mathematics Department, Universitat Rovira i Virgill, 17 pages.

(Continued)

*Primary Examiner* — Joseph D Burgess
(74) *Attorney, Agent, or Firm* — Shook, Hardy & Bacon L.L.P.

(57) ABSTRACT

A system, method, and computer-readable media are provided for facilitating clinical decision making, and in particular, facilitating treatment of a person having congestive heart failure. The method includes the step of receiving patient information for a patient. The method also includes the steps of determining whether the patient information suggests a trigger event, and upon determining a trigger event, determining at least one goal associated with the trigger event. The method also includes the steps of selecting a first plan, from a library of plans, corresponding to the goal and executing the plan, which further includes determining a solver to determine patient conditions or recommended treatments, receiving parameters for the determined solver, and preparing patient information for the determined solver. The method further includes instantiating the solver based on the received parameters and the prepared patient information, and applying the solver to determine a patient condition or recommended treatment.

18 Claims, 11 Drawing Sheets

(58) Field of Classification Search
    CPC .. G06F 19/3418; G06F 19/324; G06F 19/325;
        G06F 19/326; G06F 19/32; G06F 19/34;
        G16H 50/20; G16H 50/50; G16H 10/60;
        G16H 70/00; G16H 50/70; G16H 80/00;
        G16H 10/20; G16H 50/30
    USPC ........................................................ 705/2, 3
    See application file for complete search history.

(56) References Cited

U.S. PATENT DOCUMENTS

| | | | |
|---|---|---|---|
| 5,301,109 | A | 4/1994 | Landauer et al. |
| 5,809,494 | A | 9/1998 | Nguyen |
| 5,835,900 | A | 11/1998 | Fagg et al. |
| 6,039,688 | A | 3/2000 | Douglas et al. |
| 6,246,964 | B1 | 6/2001 | Blaunstein |
| 6,246,975 | B1 | 6/2001 | Rivonelli et al. |
| 6,247,004 | B1 | 6/2001 | Moukheibir |
| 6,397,224 | B1 | 5/2002 | Zubeldia et al. |
| 6,618,715 | B1 | 9/2003 | Johnson et al. |
| 6,654,740 | B2 | 11/2003 | Tokuda et al. |
| 6,665,669 | B2 | 12/2003 | Han et al. |
| 6,996,575 | B2 | 2/2006 | Cox et al. |
| 7,039,634 | B2 | 5/2006 | Xu et al. |
| 7,120,626 | B2 | 10/2006 | Li et al. |
| 7,249,117 | B2 | 7/2007 | Estes |
| 7,440,947 | B2 | 10/2008 | Adcock et al. |
| 7,447,643 | B1 * | 11/2008 | Olson ................ G06F 19/3418 705/2 |
| 7,496,561 | B2 | 2/2009 | Caudill et al. |
| 7,529,765 | B2 | 5/2009 | Brants et al. |
| 7,555,425 | B2 | 6/2009 | Oon |
| 7,558,778 | B2 | 7/2009 | Carus et al. |
| 7,617,078 | B2 | 11/2009 | Rao et al. |
| 7,640,171 | B2 | 12/2009 | Gendron et al. |
| 7,657,540 | B1 | 2/2010 | Bayliss |
| 7,668,820 | B2 | 2/2010 | Zuleba |
| 7,720,846 | B1 | 5/2010 | Bayliss |
| 7,831,423 | B2 | 11/2010 | Schubert |
| 7,844,449 | B2 | 11/2010 | Lin et al. |
| 7,844,566 | B2 | 11/2010 | Wnek |
| 7,853,456 | B2 | 12/2010 | Soto et al. |
| 7,865,373 | B2 | 1/2011 | Punzak et al. |
| 7,899,764 | B2 | 3/2011 | Martin et al. |
| 7,899,796 | B1 | 3/2011 | Borthwick et al. |
| 7,900,052 | B2 | 3/2011 | Jonas |
| 7,912,842 | B1 | 3/2011 | Bayliss |
| 7,933,909 | B2 | 4/2011 | Trepetin |
| 7,953,685 | B2 | 5/2011 | Liu et al. |
| 8,078,554 | B2 | 12/2011 | Fung et al. |
| 8,126,736 | B2 | 2/2012 | Anderson et al. |
| 8,160,895 | B2 | 4/2012 | Schmitt et al. |
| 8,165,893 | B1 | 4/2012 | Goldberg et al. |
| 8,200,505 | B2 | 6/2012 | Walker et al. |
| 8,515,777 | B1 | 8/2013 | Rajasenan |
| 8,539,424 | B2 | 9/2013 | Tetelbaum |
| 8,589,424 | B1 | 11/2013 | Patel et al. |
| 8,666,785 | B2 | 3/2014 | Baluta et al. |
| 8,838,628 | B2 | 9/2014 | Leighton et al. |
| 8,856,156 | B1 | 10/2014 | McNair et al. |
| 9,375,142 | B2 | 6/2016 | Schultz et al. |
| 9,542,647 | B1 | 1/2017 | Mirhaji |
| 9,734,146 | B1 | 8/2017 | McNair et al. |
| 10,249,385 | B1 | 4/2019 | McNair et al. |
| 10,268,687 | B1 | 4/2019 | McNair et al. |
| 2002/0032583 | A1 * | 3/2002 | Joao ................ 705/2 |
| 2002/0035486 | A1 | 3/2002 | Huyn et al. |
| 2002/0038227 | A1 | 3/2002 | Fey et al. |
| 2002/0038308 | A1 | 3/2002 | Cappi |
| 2002/0042793 | A1 | 4/2002 | Choi |
| 2002/0073138 | A1 | 6/2002 | Gilbert et al. |
| 2003/0023571 | A1 | 1/2003 | Barnhill |
| 2003/0038308 | A1 | 2/2003 | Kim |
| 2003/0163057 | A1 | 8/2003 | Flick et al. |
| 2003/0212580 | A1 | 11/2003 | Shen |
| 2004/0199332 | A1 | 10/2004 | Iliff |
| 2004/0230105 | A1 | 11/2004 | Geva et al. |
| 2005/0027562 | A1 | 2/2005 | Brown |
| 2005/0049497 | A1 | 3/2005 | Krishnan et al. |
| 2005/0119534 | A1 | 6/2005 | Trost et al. |
| 2005/0144042 | A1 | 6/2005 | Joffe et al. |
| 2006/0020465 | A1 | 1/2006 | Cousineau et al. |
| 2006/0064447 | A1 | 3/2006 | Malkov |
| 2006/0129427 | A1 | 6/2006 | Wennberg |
| 2006/0161457 | A1 | 7/2006 | Rapaport et al. |
| 2006/0173663 | A1 | 8/2006 | Langheier et al. |
| 2006/0205564 | A1 | 9/2006 | Peterson |
| 2006/0206027 | A1 | 9/2006 | Malone |
| 2006/0206359 | A1 | 9/2006 | Stang |
| 2006/0218010 | A1 | 9/2006 | Michon et al. |
| 2006/0271556 | A1 | 11/2006 | Mukherjee et al. |
| 2007/0005621 | A1 | 1/2007 | Lesh et al. |
| 2007/0026365 | A1 | 2/2007 | Friedrich et al. |
| 2007/0031873 | A1 | 2/2007 | Wang et al. |
| 2007/0094048 | A1 | 4/2007 | Grichnik |
| 2007/0106533 | A1 | 5/2007 | Greene |
| 2007/0106752 | A1 | 5/2007 | Moore |
| 2007/0233391 | A1 | 10/2007 | Milstein et al. |
| 2007/0239482 | A1 | 10/2007 | Finn et al. |
| 2007/0244724 | A1 | 10/2007 | Pendergast et al. |
| 2008/0021288 | A1 | 1/2008 | Bowman et al. |
| 2008/0046292 | A1 | 2/2008 | Myers et al. |
| 2008/0097938 | A1 | 4/2008 | Guyon et al. |
| 2008/0131374 | A1 | 6/2008 | Medich et al. |
| 2008/0133269 | A1 | 6/2008 | Ching |
| 2008/0147441 | A1 | 6/2008 | Kil |
| 2008/0172214 | A1 | 7/2008 | Col et al. |
| 2008/0172251 | A1 | 7/2008 | Reichert et al. |
| 2008/0183454 | A1 | 7/2008 | Barabasi et al. |
| 2008/0195422 | A1 | 8/2008 | Nessinger et al. |
| 2008/0243548 | A1 | 10/2008 | Cafer |
| 2008/0249376 | A1 | 10/2008 | Zaleski et al. |
| 2008/0255884 | A1 | 10/2008 | Carus et al. |
| 2008/0256006 | A1 | 10/2008 | Buscema et al. |
| 2008/0268413 | A1 | 10/2008 | Leichner |
| 2008/0275731 | A1 | 11/2008 | Rao et al. |
| 2008/0287746 | A1 | 11/2008 | Reisman |
| 2008/0288292 | A1 | 11/2008 | Bi et al. |
| 2008/0288474 | A1 | 11/2008 | Chin et al. |
| 2008/0301177 | A1 | 12/2008 | Doherty |
| 2008/0306926 | A1 | 12/2008 | Friedlander et al. |
| 2009/0006431 | A1 | 1/2009 | Agrawal et al. |
| 2009/0012928 | A1 | 1/2009 | Lussier et al. |
| 2009/0112892 | A1 | 4/2009 | Cardie et al. |
| 2009/0125333 | A1 | 5/2009 | Heywood et al. |
| 2009/0132284 | A1 | 5/2009 | Fey et al. |
| 2009/0164249 | A1 | 6/2009 | Hunt et al. |
| 2009/0259493 | A1 | 10/2009 | Venon et al. |
| 2009/0304246 | A1 | 12/2009 | Walker et al. |
| 2009/0318775 | A1 | 12/2009 | Michelson et al. |
| 2009/0319295 | A1 | 12/2009 | Kass-Hout et al. |
| 2010/0082369 | A1 | 4/2010 | Prenelus et al. |
| 2010/0088117 | A1 | 4/2010 | Belden et al. |
| 2010/0121883 | A1 | 5/2010 | Cutting et al. |
| 2010/0131438 | A1 | 5/2010 | Pandya et al. |
| 2010/0131482 | A1 | 5/2010 | Linthicum et al. |
| 2010/0131883 | A1 | 5/2010 | Linthicum et al. |
| 2010/0142774 | A1 | 6/2010 | Ben-Haim et al. |
| 2010/0145720 | A1 | 6/2010 | Reiner |
| 2010/0179818 | A1 | 7/2010 | Kelly et al. |
| 2010/0185685 | A1 | 7/2010 | Chew et al. |
| 2010/0274576 | A1 | 10/2010 | Young |
| 2010/0293003 | A1 | 11/2010 | Abbo |
| 2010/0299155 | A1 | 11/2010 | Findlay et al. |
| 2010/0324938 | A1 | 12/2010 | Ennett et al. |
| 2011/0010401 | A1 | 1/2011 | Adams et al. |
| 2011/0015937 | A1 | 1/2011 | Janas et al. |
| 2011/0046979 | A1 | 2/2011 | Tulipano et al. |
| 2011/0067108 | A1 | 3/2011 | Hoglund |
| 2011/0077973 | A1 | 3/2011 | Breitenstein et al. |
| 2011/0087501 | A1 | 4/2011 | Severin |
| 2011/0093467 | A1 | 4/2011 | Sharp et al. |
| 2011/0119089 | A1 | 5/2011 | Carlisle |
| 2011/0161110 | A1 | 6/2011 | Mault |

(56) References Cited

U.S. PATENT DOCUMENTS

| | | | |
|---|---|---|---|
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | McDonald et al. |
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | Mcerlane |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2013/0006911 A1 | 1/2013 | Christie, IV et al. |
| 2013/0023434 A1 | 1/2013 | Van |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132312 A1 | 5/2013 | Lee et al. |
| 2013/0132323 A1 | 5/2013 | Soto et al. |
| 2013/0197938 A1 | 8/2013 | Bayouk et al. |
| 2013/0245389 A1 | 9/2013 | Schultz et al. |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | Mcnair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0124269 A1 | 5/2017 | Mcnair et al. |

FOREIGN PATENT DOCUMENTS

| | | | |
|---|---|---|---|
| WO | 2012/122196 A2 | 9/2012 |
| WO | 2012122195 A2 | 9/2012 |

OTHER PUBLICATIONS

Kang, et al.: Mining Based Decision Support Multi-agent System for Personalized e-Healthcare Service*, School of Computer Engineering, Sungkyunkwan University, 10 pages.
Mabry, et al.: Clinical Decision Support with IM-Agents and ERMA Multi-agents, Department of Computer Science and Emergency Medicine, 6 pages.
United States Patent and Trademark Office: Preinterview First Action Interview referencing U.S. Pat. No. 7,447,643; U.S. Appl. No: 13/250,072; dated Jan. 3, 2013, 8 pages.
Final Office Action dated Jun. 2, 2014 in U.S. Appl. No. 13/269,262, 14 pages.
First Action Interview Pre-Interview Communication dated Feb. 10, 2014 in U.S. Appl. No. 13/269,244, 5 pages.
First Action Interview Office Action dated Jun. 17, 2014 in U.S. Appl. No. 13/269,244, 5 pages.
First Action Interview Pre-Interview Communication dated Mar. 28, 2013 in U.S. Appl. No. 13/269,262, 4 pages.
Non-Final Office Action dated Dec. 5, 2014 in U.S. Appl. No. 13/269,244, 18 pages.
First Action Interview Office Action dated Oct. 11, 2013 in U.S. Appl. No. 13/269,262, 5 pages.
Notice of Allowance dated Jun. 4, 2014 in U.S. Appl. No. 13/645,896, 12 pages.
Non-Final Office Action dated May 22, 2015 in U.S. Appl. No. 13/963,732, 14 pages.
Final Office Action dated Jul. 13, 2015 in U.S. Appl. No. 13/269,244, 21 pages.
First Action Interview Preinterview Communication dated Oct. 4, 2012 in U.S. Appl. No. 12/982,143, 5 pages.
First Action Interview Preinterview Communication dated Sep. 26, 2012 in U.S. Appl. No. 12/982,131, 4 pages.
First Action Interview Preinterview Communication dated Sep. 26, 2012 in U.S. Appl. No. 12/982,137, 4 pages.
First Action Interview Office Action dated Nov. 21, 2012 in U.S. Appl. No. 12/982,143, 7 pages.
Final Office Action dated Apr. 24, 2013 in U.S. Appl. No. 12/982,131, 25 pages.
Final Office Action dated May 1, 2013 in U.S. Appl. No. 12/982,143, 22 pages.
Final Office Action dated May 8, 2013 in U.S. Appl. No. 12/982,137, 22 pages.
Non-Final Office Action dated Oct. 2, 2013 in U.S. Appl. No. 12/982,143, 24 pages.
Notice of Allowance dated Nov. 14, 2013 in U.S. Appl. No. 12/982,137, 15 pages.
First Action Interview Preinterview Communication dated Dec. 27, 2013 in U.S. Appl. No. 13/647,187, 7 pages.
First Action Interview Office Action dated Apr. 3, 2014 in U.S. Appl. No. 13/647,187, 10 pages.
Non-Final Office Action dated Dec. 20, 2013 in U.S. Appl. No. 12/982,131, 19 pages.
Final Office Action dated Sep. 29, 2014 in U.S. Appl. No. 13/647,187, 21 pages.
Final Office Action dated Nov. 7, 2014 in U.S. Appl. No. 12/982,131, 17 pages.
Notice of Allowance dated Apr. 9, 2015 in U.S. Appl. No. 12/982,131, 12 pages.
International Search Report and Written Opinion dated Nov. 26, 2014 in Application No. PCT/US2014/050735, 11 pages.
First Action Interview Preinterview Communication dated Jun. 30, 2015 in U.S. Appl. No. 14/147,978, 5 pages.
First Action Interview Preinterview Communication dated Jun. 30, 2015 in U.S. Appl. No. 14/148,028, 5 pages.
First Action Interview Preinterview Communication dated Jul. 17, 2015 in U.S. Appl. No. 14/148,039, 5 pages.
First Action Interview Preinterview Communication dated Jul. 30, 2015 in U.S. Appl. No. 14/147,991, 5 pages.
First Action Interview Preinterview Communication dated Aug. 11, 2015 in U.S. Appl. No. 14/148,059, 5 pages.
First Action Interview Pre-Interview Communication dated Aug. 11, 2015 in U.S. Appl. No. 14/148,002, 5 pages.
First Action Interview Pre-Interview Communication dated Aug. 14, 2015 in U.S. Appl. No. 14/148,050, 5 pages.
Non-Final Office Action dated Aug. 5, 2015 in U.S. Appl. No. 14/477,284, 11 pages.
Non-Final Office Action dated Aug. 31, 2015 in U.S. Appl. No. 13/647,187, 18 pages.
Non-Final Office Action dated Sep. 1, 2015 in U.S. Appl. No. 13/874,961, 33 pages.
Murat Sariyar and Andreas Borg, The Recordlinkage Package: Detecting Errors in Data, Dec. 2010, The R Journal vol. 212, pp. 61-67.
Christian Roever, Package 'bspec', Feb. 21, 2013, r-project.org, pp. 1-27.
Abbott A, Tsay A. Sequence Analysis and Optimal Matching Methods in Sociology, Review and Prospect. Sociol Meth Res 2000; 29:3-33.
Agrawal R, et al. 'Fast Discovery of Association Rules.' In Fayyad U, et al., eds., Advances in Knowledge Discovery and Data Mining, pp. 307-328. Menlo Park, AAAI Press, 1996.

(56) References Cited

OTHER PUBLICATIONS

Berchtold A, Raftery A. The Mixture Transition Distribution Model for High-Order Markov Chains and Non-Gaussian Time Series. Stat Sci 2002;17:328-56.
Billari F, et al. Timing, Sequencing, and quantum of Life Course Events: A Machine-Learning Approach. Eur J Pop 2006;22:37-65.
Deville J, Saporta G. Correspondence Analysis with an Extension Towards Nominal Time Series. J Econometrics 1983;22:169-89.
Dijkstra W, Taris T. Measuring the Agreement Between Sequences. Sociol Meth Res 1995;24:214-31.
Dvorak J, et al. Risk Factor Analysis for Injuries in Football Players: Possibilities for a Prevention Program. Am J Sports Med. 2000;28:S69-74.
Dvorak J, Junge A. Football Injuries and Physical Symptoms: A Review of the Literature. Am J Sports Med 2000;28:S3-9.
Han J-W, et al. Frequent Pattern Mining: Current status and future directions. Data Mining and Knowledge Discovery 2007;15:55-86.
Junge A, Dvorak J. Soccer Injuries: A Review on Incidence and Prevention. Sports Med. 2004;34:929-38.
Nielsen A, Yde J. Epidemiology and Traumatology of Injuries in Soccer. Am J Sports Med 1989;17:803-7.
Zaki M. Spade: An Efficient Algorithm for Mining Frequent Sequences. Machine Learning 2001;42:31-60.
Huyse, Frits; De Jonge, Peter; Slaets, Joris; Herzog, Thomas; Lobo, Antonio; Lyons, John, Opmeer, Brent; Stein, Barbara; Arolt, Volker; Balogh, Nandor; Cardoso, Graca; Fink, Per; Rigatelli, Marco; Compri—An Instrument to Detect Patients With Complex Care Needs; Psychosomatics 42:3,May-Jun. 2001; 7 pages.
Berry, Leonard; Rock, Beth; Houskamp, Beth; Brueggeman, Joan; Tucker, Lois; Care Coordination for Patients With Complex Health Profiles in Inpatients and Outpatient Settings; Mayo Clinic Proceedings; www.mayoclinicproceedings.org; Jan. 11, 2013; 11 pages.
Cohen, Eyal; Lacombe-Duncan, Ashley; Spalding, Karen; Macinnis, Jennifer; Nicholas, David; Narayanan, Unni; Gordon, Michelle; Margolis, Ivor; Friedman, Jeremy; Integrated Complex Care Coordination for Children With Medical Complexity: A Mixed-Methods Evaluation of Tertiary Care-Community Collaboration; BioMed Central the Open Access Publisher; www.biomedcentral.com/1472-6963/12/366; Oct. 23, 2012; 23 pages.
Final Office Action dated Dec. 4, 2015 in U.S. Appl. No. 13/963,732, 21 pages.
First Action Interview Office Action dated Dec. 3, 2015 in U.S. Appl. No. 14/147,978, 8 pages.
First Action Interview Office Action dated Jan. 20, 2016 in U.S. Appl. No. 14/147,991, 8 pages.
First Action Interview Office Action dated Jan. 15, 2016 in U.S. Appl. No. 14/148,002, 8 pages.
First Action Interview Office Action dated Dec. 22, 2015 in U.S. Appl. No. 14/148,028, 8 pages.
First Action Interview Office Action dated Nov. 19, 2015 in U.S. Appl. No. 14/148,039, 8 pages.
First Action Interview Preinterview Communication dated Nov. 19, 2015 in U.S. Appl. No. 14/148,046, 5 pages.
First Action Interview Office Action dated Jan. 22, 2016 in U.S. Appl. No. 14/148,050, 8 pages.
First Action Interview Office Action dated Dec. 17, 2015 in U.S. Appl. No. 14/148,059, 8 pages.
First Action Interview Office Action dated Jan. 6, 2016 in U.S. Appl. No. 14/148,020, 8 pages.
First Action Interview Preinterview Communication dated Aug. 13, 2015 in U.S. Appl. No. 14/148,020, 5 pages.
Ohno-Machado, Lucile; "Realizing the full potential of electronic health records: the role of natural language processing", Sep. 2011, Journal of American Medical Information Association, vol. 18 No. 5, p. 539.
Non-Final Office Action dated May 18, 2017 in U.S. Appl. No. 14/147,978, 29 pages.
Non-Final Office Action dated Jun. 6, 2017 in U.S. Appl. No. 14/148,059, 30 pages.
Final Office Action dated Jun. 16, 2017 in U.S. Appl. No. 14/209,568, 20 pages.
First Action Interview Preinterview Communication dated Jun. 21, 2017 in U.S. Appl. No. 14/281,593, 4 pages.
Non-Final Office Action dated Jun. 21, 2017 in U.S. Appl. No. 14/148,039, 34 pages.
Non-Final Office Action dated Jun. 28, 2017 in U.S. Appl. No. 14/148,046, 31 pages.
Non-Final Office Action dated Jul. 5, 2017 in U.S. Appl. No. 14/147,991, 36 pages.
Non-Final Office Action dated Jul. 24, 2017 in U.S. Appl. No. 14/148,020, 22 pages.
Supplemental Notice of Allowability dated Jul. 26, 2017 in U.S. Appl. No. 14/477,284, 6 pages.
Final Office Action dated Jul. 27, 2017 in U.S. Appl. No. 13/647,187, 23 pages.
Non-Final Office Action dated Jul. 31, 2017 in U.S. Appl. No. 14/148,060, 24 pages.
Non-Final Office Action dated Aug. 10, 2017 in U.S. Appl. No. 14/148,002, 26 pages.
Final Office Action dated Sep. 23, 2016 in U.S. Appl. No. 14/148,059, 27 pages.
Final Office Action dated Sep. 26, 2016 in U.S. Appl. No. 13/269,244, 35 pages.
Final Office Action dated Oct. 3, 2016 in U.S. Appl. No. 14/148,046, 26 pages.
Final Office Action dated Nov. 2, 2016 in U.S. Appl. No. 13/874,961, 18 pages.
Non-Final Office Action dated Jan. 13, 2017 in U.S. Appl. No. 13/647,187, 20 pages.
Final Office Action dated Feb. 16, 2017 in U.S. Appl. No. 14/175,750, 18 pages.
European Search Report dated Mar. 13, 2017 in European Patent Application No. 14835964, 9 pages.
Final Office Action dated May 12, 2017 in U.S. Appl. No. 13/963,732, 20 pages.
Kiran, R. Uday, and P. Krishna Re. "An improved multiple minimum support based approach to mine rare association rules." Computational Intelligence and Data Mining, 2009. CIDM'09. IEEE Symposium on. IEEE, 2009.
First Action Interview Office Action dated Sep. 6, 2017 in U.S. Appl. No. 14/281,593, 7 pages.
Non-Final Office Action dated Sep. 21, 2017 in U.S. Appl. No. 14/148,046, 27 pages.
Non-Final Office Action dated Sep. 22, 2017 in U.S. Appl. No. 14/175,750, 10 pages.
First Action Interview Pre-Interview Communication dated Dec. 8, 2017 in U.S. Appl. No. 14/792,736, 22 pages.
Final Office Action dated Dec. 11, 2017 in U.S. Appl. No. 14/148,059, 27 pages.
Non-Final Office Action dated Dec. 27, 2017 in U.S. Appl. No. 13/963,732, 18 pages.
Final Office Action dated Jan. 4, 2018 in U.S. Appl. No. 14/147,991, 35 pages.
Final Office Action dated Jan. 5, 2018 in U.S. Appl. No. 14/148,028, 44 pages.
Final Office dated Jan. 18, 2018 in U.S. Appl. No. 14/147,978, 28 pages.
Final Office Action dated Jan. 26, 2018 in U.S. Appl. No. 14/148,039, 33 pages.
Final Office Action dated Feb. 16, 2018 in U.S. Appl. No. 14/281,593, 15 pages.
Final Office Action received for U.S. Appl. No. 14/555,058, dated Sep. 7, 2018, 19 pages.
Final Office Action received for U.S. Appl. No. 14/792,736, dated Oct. 15, 2018, 18 pages.
Non-Final Office Action received for U.S. Appl. No. 14/147,978, dated Sep. 28, 2018, 29 pages.
Notice of Allowance received for U.S. Appl. No. 13/874,961, dated Oct. 15, 2018, 9 pages.
Final Office Action received for U.S. Appl. No. 14/148,046, dated May 1, 2018, 31 pages.

(56) References Cited

OTHER PUBLICATIONS

Hawkins et al., "A Prospective Epidemiological Study of Injuries in Four English Professional Football Clubs", British Journal of Sports Medicine, vol. 33, 1999, pp. 196-203.
Non-Final Office Action received for U.S. Appl. No. 14/555,058, dated Dec. 29, 2017, 13 pages.
Non-Final Office Action received for U.S. Appl. No. 13/647,187, dated Apr. 13, 2018, 27 pages.
Non-Final Office Action received for U.S. Appl. No. 14/148,059, dated Jun. 28, 2018, 27 pages.
Non-Final Office Action received for U.S. Appl. No. 15/392,928, dated May 3, 2018, 15 pages.
Non-Final Office Action received for U.S. Appl. No. 14/209,568, dated Mar. 2, 2018, 23 pages.
Aronson, Alan R., "MetaMap: Mapping Text to the UMLS Metathesaurus", 2006, pp. 1-26.
Final Office action received for U.S. Appl. No. 13/647,187, dated Dec. 14, 2018, 28 pages.
Non-Final Office Action received for U.S. Appl. No. 14/147,991, dated Nov. 27, 2018, 37 pages.
International Preliminary Report on Patentability dated Feb. 25, 2016 in Application No. PCT/US2014/050735, 9 pages.
Final Office Action dated Jun. 28, 2016 in U.S. Appl. No. 13/874,961, 19 pages.
Final Office Action dated Jul. 1, 2016 in U.S. Appl. No. 14/147,978, 25 pages.
Final Office Action dated Jul. 14, 2016 in U.S. Appl. No. 14/148,028, 28 pages.
Final Office Action dated Jul. 20, 2016 in U.S. Appl. No. 14/148,039, 32 pages.
Non-Final Office Action dated Jul. 26, 2016 in U.S. Appl. No. 13/963,732, 16 pages.
Final Office Action dated Jul. 29, 2016 in U.S. Appl. No. 14/148,020, 23 pages.
Notice of Allowance dated Aug. 2, 2016 in U.S. Appl. No. 14/477,284, 7 pages.
Final Office Action dated Aug. 15, 2016 in U.S. Appl. No. 14/147,991, 34 pages.
First Action Interview Office Action dated Aug. 17, 2016 in U.S. Appl. No. 14/175,750, 5 pages.
Non-Final Office Action dated Sep. 1, 2016 in U.S. Appl. No. 14/209,568, 12 pages.
Final Office Action dated Sep. 8, 2016 in U.S. Appl. No. 14/148,002, 24 pages.
Final Office Action dated Sep. 9, 2016 in U.S. Appl. No. 14/148,050, 23 pages.
Non-Final Office Action received for U.S. Appl. No. 14/148,059, dated Apr. 26, 2019, 28 pages.
Non-Final Office Action received for U.S. Appl. No. 14/792,736, dated Apr. 11, 2019, 18 pages.
Non-Final Office Action received for U.S. Appl. No. 14/982,982, dated May 14, 2019, 9 pages.
First Action Interview Office Action dated Feb. 26, 2016 in U.S. Appl. No. 14/148,046, 8 pages.
Non-Final Office Action dated Mar. 10, 2016 in U.S. Appl. No. 13/269,244, 28 pages.
First Action Interview Preinterview Communication dated Mar. 10, 2016 in U.S. Appl. No. 14/175,750, 4 pages.
Notice of Allowance dated Mar. 11, 2016 in U.S. Appl. No. 14/477,284, 6 pages.
Final Office Action dated May 3, 2016 in U.S. Appl. No. 13/647,187, 19 pages.
Non-Final Office Action received for U.S. Appl. No. 14/148,046, dated Jun. 24, 2019, 27 pages.
Non Final Office Action received for U.S. Appl. No. 14/555,058, dated Jun. 25, 2019, 20 pages.
Arpaia et al., "Multi-Agent Remote Predictive Diagnosis of Dangerous Good Transports", Instrumentation and Measurement Technology Conference, Proceedings of IEEE, May 17-19, 2005, pp. 1685-1690.
Non-Final Office Action received for U.S. Appl. No. 13/963,732, dated Jul. 11, 2019, 13 pages.

* cited by examiner

DRUGS

| NAME | DOSE | UNIT | FREQUENCY | ROUTE | QUANTITY | CONCEPT/KEYWORD | | TEXT |
|---|---|---|---|---|---|---|---|---|
| | | | | | | QUANTITY | | |
| HCTZ | 50 | MG | BID | | | HYDRODIURIL 50MG | | |
| METOPROLOL SR | 50 | MG | QD | | | HYDRODIURIL 50MG | | |
| ROSIGLITAZONE | 4 | MG | | | | ROSIGLITAZONE+METFORMIN 4 MG | | |
| SPIRONOLACTONE | | | | | | SPIRONOLACTONE | | |
| VALZARTAN | | | | | | VALSARTAN | | |
| AMIODARONE | 2 | | | | | AMIODARONE | | |
| METFORMIN | 2 | | | | | METFORMIN | | |

| LABS | | | | |
|---|---|---|---|---|
| NAME | VALUE | UM | | DATE |
| BP | 155/95 | MG | | |
| ATRIAL | 188 | | | |
| BLOOD GLUCOSE | 400 | MG/DL | | |
| SODIUM | 130 | MEQ/L | | |
| POTASSIUM | 3.4 | MEQ/L | | |
| HBA1C | 8.5 | % | | |
| WEIGHT | 95 | KG | | |
| BMI | 30 | KG/M2 | | |
| WAIST/HIP RATIO | 0.98 | | | |

| SAMPLE | STATE | CONDITION |
|---|---|---|
| 001 | NORMALTENSION | BP60 1 |
| 002 | HYPERTENSION | BP61 1 |
| 003 | HYPERTENSION | BP62 1 |
| 004 | HYPERTENSION | BP63 1 |

| SAMPLE | DRUG | OBJECT | COEF |
|---|---|---|---|
| 001 | HCTZ | | 1.5 |
| 002 | SPIRONOLACTONE | | 1.8 |
| 003 | LIGHOPRIL | | 1.7 |
| 004 | VALSARTAN | | 2.0 |

| SAMPLE MATRIX | | | | | |
|---|---|---|---|---|---|
| 002 | 001 | 1 | 1 | HCTZ | 12.5 MG | ND |
| 002 | 001 | 2 | 2 | HCTZ | 12.5 MG | BID |
| 002 | 002 | 1 | 2 | SPIRONOLACTONE | 50 MG | IPO QD |
| 002 | 002 | 2 | 3 | SPIRONOLACTONE | 100 MG | IPO QD |

COMPUTERIZED SYSTEMS AND METHODS FOR FACILITATING CLINICAL DECISION MAKING

CROSS-REFERENCE TO RELATED APPLICATIONS

This Application claims the benefit of priority to U.S. Provisional Application No. 61/389,053, filed Oct. 1, 2010, which is expressly incorporated by reference herein in its entirety.

BACKGROUND

Healthcare is extremely complex due to disparate systems and distributed data and the need to be efficient and adaptable. The mission of integrating decision support within health care applications is becoming even more challenging and daunting in a distributed environment due to further disparate data sources and ever changing requirements and expectations. For example, patient scheduling is complex due to large numbers of tasks that need to be completed by multiple departments distributed throughout. Coordination by wide number of care givers with different skill sets and functions is problematic.

Inpatients, outpatients, nurses, physicians, med techs, managers and others are distributed throughout the healthcare process. Shifts in health care towards shared patient-provider decision making and managed care add further complexity. Patient records are distributed across multiple locations, in various digital and physical formats, and the coordination of activities to be performed for health care in community care is increasingly complex. Moreover, there are increasing demands and needs to reduce errors in diagnosis and treatment, to provide health care to distributed locations, and to provide and promote better methods for education and training.

There are also increasing demands to keep up with new medicine, complex treatments and techniques, to find relevant data faster and simpler to assist care givers. There is an increasing need to control usage of restricted medicine and treatments, to be responsive to changes in environment and missing and incomplete data, and to provide better monitoring status of patient and co-operative decision making with the care giver. There is also a need to facilitate decision-making where uncertainty exists in diagnosis, therapy, drug prescription and testing.

Rule engines may be used for solving some of these problems when only simple scenarios exist or using only limited information. But rules engines become unmanageable when a rules library gets excessively large due to overlapping rules, contradictory rules, difficulties in rule verification and overall view of the active rules and support for multiple disparate rule engines. Such systems can result in less-than-optimized solutions, conflicting orders, or are simply unable to handle more complex scenarios such as patients having multiple conditions, when conditions are interdependent.

SUMMARY

A system, methods and computer-readable media are provided for facilitating clinical decision making, and in particular, facilitating treatment of a person having congestive heart failure. In embodiments, a method for clinical decision making is provided. The method includes the step of receiving patient information for a patient. The method also includes the steps of determining whether the patient information suggests a trigger event, such as information suggesting possible heart failure, for example, and upon determining a trigger event, determining at least one goal associated with the trigger event. The method also includes the steps of selecting a first plan, from a library of plans, corresponding to the goal and executing the plan, which further includes determining a solver to determine patient conditions or recommended treatments, receiving parameters for the determined solver, and preparing patient information for the determined solver. The method further includes instantiating the solver based on the received parameters and the prepared patient information, and applying the solver to determine a patient condition or recommended treatment. In one embodiment, the method further includes invoking an expert rules engine to determine an action or disposition specific to the patient based on the determined patient condition or recommended treatment.

BRIEF DESCRIPTION OF THE DRAWINGS

The present invention is described in detail below with reference to the attached drawing figures, wherein:

FIG. 6A depicts an illustrative discretized patient information suitable for use with one or more solvers to determine a condition or recommended treatment in accordance with embodiments of the invention;

FIG. 6B depicts illustrative solver content-parameters ("content tables") suitable for use with one or more solvers to determine a condition or recommended treatment in accordance with embodiments of the invention;

DETAILED DESCRIPTION

Figure 1A:
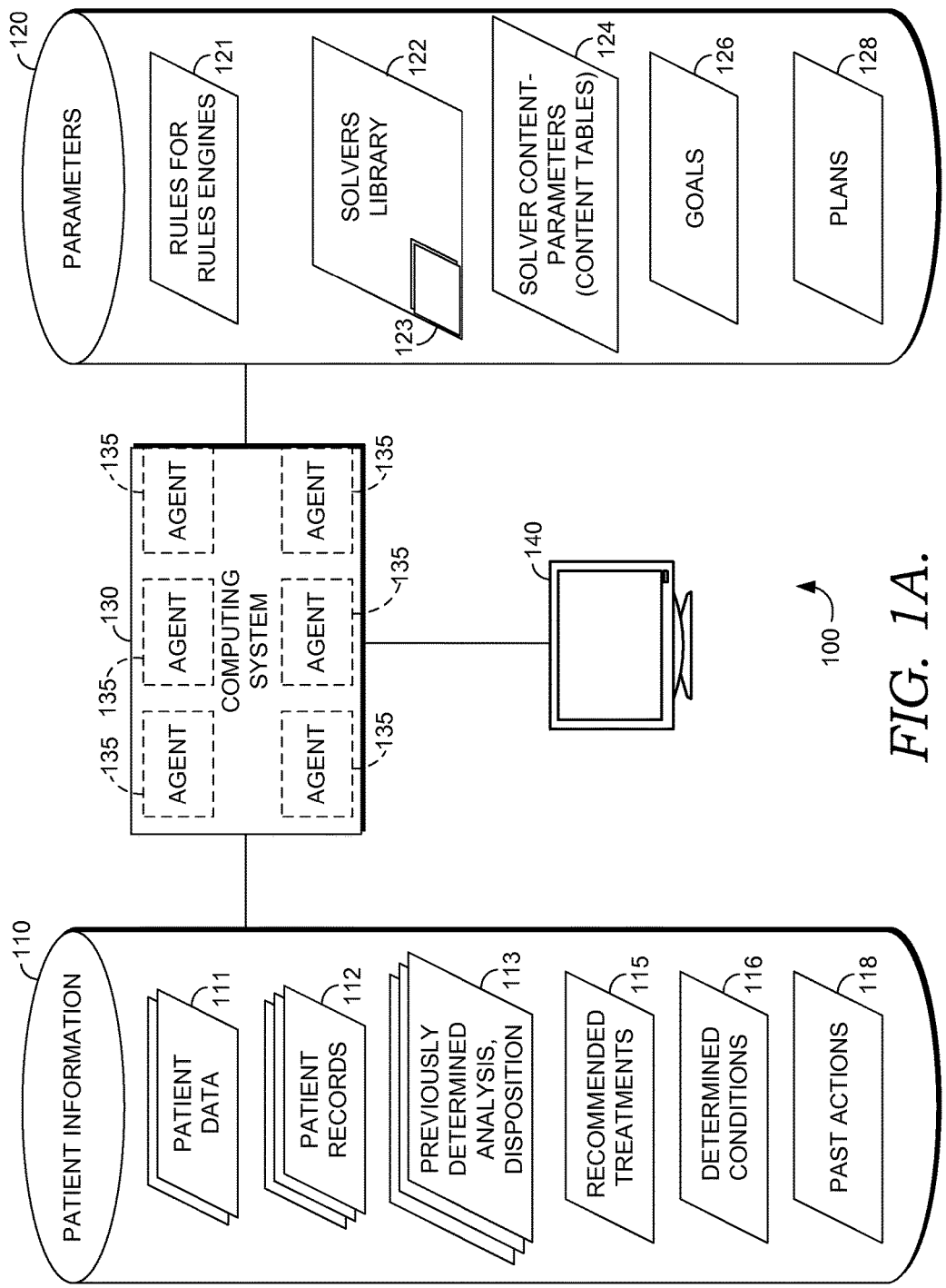
FIG. 1A depicts aspects of an illustrative operating environment suitable for practicing embodiments of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

A better framework is provided herein for building, testing, deploying and integrating decision support into health care applications is necessary to meet industry needs and demand. The solution, described herein, to the problems discussed above is able to more accurately and quickly provide prioritized orders, expert-information to the healthcare provider. A virtual decision support operating system is also provided to transform health care applications into the next generation applications which the ability to learn from past and current behaviors and to adapt and evolve in a dynamic environment. Specifically, the system and methods described below facilitate clinical decision making by employing solvers, which may include software agents, to apply decision processing structures and techniques that are tailored to the patient.

Embodiments of the present invention provide a computerized system, methods, and computer-readable media for use in facilitating clinical decision making, and in particular, knowledge integration for facilitating treatment of a person having congestive heart failure. For example, decision making by a health care provider is facilitate by providing a decision support agent framework with heuristic, adaptive, self-optimizing, ubiquitous and learning capabilities for decomposing complex problems into manageable, distributable tasks with context awareness.

By way of example and not limitation, a health care provider might be able to more quickly and with greater accuracy diagnose, provide treatment, order testing, or specify other actions for a patient suffering from any combination of congestive heart failure, arterial fibrillation, diabetes, hypertension, or coagulopathy in various degrees. One or more patient-specific solvers is instantiated and invoked to determine conditions and recommended treatments of the patient. The solver type and architecture are determined based on the patient information and independent content parameters, which we refer to as content tables, which specify information regarding conditions, drugs, and contra-indications. Other parameters may be used by to instantiate a particular solver and may be updated by physicians or experts independently of the patient.

In one embodiment, a finite state machine solver is instantiated such that states are determined by the patient information and the state transitions are determined by the content tables. In one embodiment, multiple solvers are instantiated, for example as the finite state machine, described in the preceding embodiment, is evaluated, each evaluated state may be passed to a second solver such as a mixed integer linear solver. In one embodiment, the finite state machine returns the actual state for each clinical condition, which is then passed on to the mixed integer linear solver as parameters, to apply the mixed integer solver based on the clinical state, and the content tables. In one embodiment, a solver is instantiated by a software agent, which we refer to as a planning-agent. In another embodiment, the solver is a software-agent and may be leveraged by another agent such as a planning agent. An exemplary operating environment for the present invention is described in connection to FIGS. 1A-1C, and relates generally to the description of a multi-agent system, for use in some embodiments of the invention, and described below in connection to FIGS. 1A and 1B.

Referring to the drawings in general, and initially to FIG. 1A in particular, an exemplary operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, environment 100 includes computer system 130. In some embodiments, computing system 130 is a multi-agent computing system with one or more agents 135, as shown in FIG. 1A and described in greater detail below. But it will be appreciated that computing system 130 may also take the form of a single agent system or a non-agent system. Computing system 130 may be a distributed computing system, a centralized computing system, a single computer such as a desktop or laptop computer or a networked computing system.

In some embodiments of our invention, computer system 130 is a multi-agent computer system with agents 135. Multi-agent system 130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents 135 based on beliefs, capabilities and choices that communicate via declarative messaging and use abstractions to allow for future adaptations and flexibility. An agent 135 has its own thread of control which promotes the concept of autonomy.

Embodiments using multi-agent system 130 provide capabilities to adapt the frequency and messages used for communication between the system 130 and one or more users 140, based on changes to the environment and provide capabilities to filter out noisy data, thereby providing more flexible and adaptable decision making abilities. In some embodiments, this is accomplished by using leveraging preceptors and effectors. Preceptors or sensors, which in some embodiments may be agents, detect changes in an operating environment and pass this information to the agent system. Effectors, which in some embodiments may be agents 135, respond directly to changes in an operating environment and consider goals and alternatives prior to implementing a change to the environment.

Embodiments using multi-agent system 130 further have the capability of supporting intelligent information retrieval and filter out noisy data and utilize heuristics to narrow down a search space to assist in solving complex problems. The multi-agent system 130 facilitates designing individual agent behaviors and their interactions with other agents 135 and with users 140. In some embodiments, agents 135 encoded with both declarative and procedural knowledge and can therefore learn by means of exploration of knowledge and imitation of other agents, for example, by leveraging aggregation of bottom-up and top-down modeling. In some embodiments, the agent system 130 accepts an abstract workflow and converts it into an actual executable workflow, by for example, using contract and negotiation in multi-agent system 130. The executable workflow may then leverage agents to run the actual workflow.

Embodiments using multi-agent system 130 coordinate the actions of the agents 135 to cooperate to achieve common objectives, and negotiate to resolve conflicts, which allows for adaptability, flexibility, and organizational relationships. The transformation of heterogeneous knowledge and content into homogeneous knowledge and content is an important trait of the multi-agent system to provide interoperability. The multi-agent system 130 operates to achieve its goals while still interacting with agents, including agents outside of the multi-agent system 130 (not shown) and users 140 at a higher degree of flexibility. As an example, in one embodiment a multi-agent system 130 can be utilized to efficiently optimize a reverse auction scenario, since the ability to negotiate and cooperate among agents are inherent properties of the multi-agent system. A reverse auction process allows a "buyer" to negotiate the best value with multiple "sellers." This analogy applies to the health care setting, which must optimize its resources and deliver the most optimal care.

In some embodiments, agents 135 continually monitor events to proactively detect problems and leverage reasoning to react and dynamically alter a plan. Practical reasoning involves managing conflict resolution where the relevant considerations are provided by the agent's desires about what the agent believes. This involves deliberation by deciding what state of affairs the agent wants to achieve using intentions and by means-end reasoning which is how to achieve those desires using plans. By way of background, an intention is stronger than a desire and planning achieves designated goals. Thus in one embodiment, a basic planning module consists of goals and intentions to be achieved, actions that can be performed, and a representation of the environment. These plans can thus handle priorities, uncertainty and rewards to influence the actual plans.

Continuing with FIG. 1A, system 130 is communicatively coupled to patient information 110 and parameters 120, and user interface 14, described below. System 130 performs processing on patient information 110 and parameters 120. In some embodiments, system 130 includes one or more agents 135, which process patient information 110 using parameters 120 to determine goals, plans, patient actions, orders, patient conditions and recommended treatments, or invoke other agents, such as agent solvers, to perform these determinations. For example, system 130 may receive patient data 111 in the form of a natural-language narrative, such as a physicians note, and invoke an data-extraction agent, from a solvers library 122, to extract discrete data from the note. System 130 may then use the discrete data and content tables 124 to instantiate and apply another solver agent, from solvers library 122, such as a finite state machine solver agent, to determine a patient's condition and recommended treatments. Finally, upon determining a patient's condition and recommended treatments, system 130 might invoke an expert rules engine using rules 121 to determine specific actions or a disposition for the patient, based on the determined conditions and recommended treatments.

System 130 is executed by or resides on one or more processors operable to receive instructions and process them accordingly, and may be embodied as a single computing device or multiple computing devices communicatively coupled to each other. In one embodiment processing actions performed by system 130 are distributed among multiple locations such as a local client and one or more remote servers. In another embodiment, system 130 resides on a computer, such as a desktop computer, laptop, or tablet computer. Example embodiments of system 130 reside on a desktop computer, a cloud-computer or distributed computing architecture, a portable computing device such as a laptop, tablet, ultra-mobile P.C., or a mobile phone.

Coupled to system 130 is display for user 140. Display for a user 140 provides a presentation capability and user interface to facilitate communication with users. Using display for a user 140, a user may view determined results about a patient or provide additional information such as patient information, in one embodiment. Display for a user 140 may be a single device or a combination of devices and may be stationary or mobile. In some embodiments, a user interface on display device takes the forms of one or more presentation components such as a monitor, computing screen, projection device, or other hardware for displaying output. In some embodiments, a user interface on display device takes the form of one or more presentation components with user input components, such as a remote computer, a desktop computer, laptop, pda, mobile phone, ultra-mobile pc, computerized physician's clipboard, or similar device. In some embodiments, data elements and other information may be received from display device by a user 140. Queries may be performed by users 140; additional orders, tests, feedback or other information may be provided through the display device to user 140.

Environment 100 includes data store 110 which includes patient information and data store 120 which includes parameters. In some embodiments, data stores 110 and 120 comprises networked storage or distributed storage including storage on servers located in the cloud. Thus, it is contemplated that for some embodiments, the information stored in data stores 110 or 120 is not stored in the same physical location. For example, in one embodiment, one part of data store 110 includes one or more USB thumb drives or similar portable data storage media. Additionally, information stored in data store 110 and 120 can be searched, queried, analyzed using system 130 or user interface 140, which is further described below.

Patient data store 110 comprises information specific to a patient including, which in some instances may include incomplete, outdated, uncertain, overlapping, and conflicting information. Moreover the information may exist in a variety of formats including for example, narratives and discretized data. In one embodiment, patient information includes patient data 111, patient records 112, previously determined analysis or disposition 113, which are associated with the patient, recommended treatments 115, previously determined patient conditions 116, and past actions 118 performed for the patient. In some embodiments, patient data 111 can include lab results, real-time information such as data provided by a physician, including information based on observation or a patient's explanation, information provided by a sensor (e.g., blood pressure or heart rate), or other patient data. In some embodiments, patent records 112 can include electronic medical records ("EMR"), health information exchange ("HIE"), personal health record ("PHR"), patient claims, and other health-related records associated with a patient.

Previously determined analysis and dispositions 115 include information relating to previous analyses performed on a patient and previous dispositions determined for the patient, including previous analyses and dispositions determined by way of the multi-agent system, in some embodiments. Multiple-agent system 130 may handle a complex problem, such as determining patient conditions or recommended treatments. Each of the agents 135 may generate multiple analysis and/or disposition for the patient. In this embodiment, a degree of statistical certainty about a determined disposition of analysis may be arrived at by correlating each of the separate analyses and/or dispositions. More specifically, if separate agents 135 each determine substantially the same analysis or disposition using different levels of patient information, then there may be a higher degree of confidence that the analysis or disposition is accurate, given the available patient information.

Recommended treatments 115 include currently and previously recommended treatments for a patient. In one embodiment, this information includes time-related data associated with the time that the recommended treatment was determined, as well as an indication of whether the recommended treatment has been acted upon. In one embodiment, recommended treatments 115 also specify how the recommended treatment was determined, including for example, available patient information, the type of solver that was applied, and the resulting patient conditions, thereby enabling a health care provider to query the recommended treatments to see how a particular treatment was determined or to generate a report.

Past actions 118 includes previous actions determined by the multi-agent system 130. Similarly to what is described above in connection to recommended treatments 115, past actions 118 may include time-information associated with the time that the action was determined or executed, or may also specify how the action was determined or executed.

Data store 120 comprises parameters and information associated with the multi-agent system 130. Although depicted as working with a multi-agent system, in one embodiment, data store 120 works with single-agent system parameters and information, or non-agent system parameters and information. In one embodiment, data store 120 includes rules for a rules engine 121, solvers library 122, solver-content parameters ("content tables") 124, goals 126, and plans 128. Rules for a rules engine 121 include a set of rules or library of rules. In one embodiment, rules 121 are usable by an expert rules-engine, such as an agent 135 in multi-agent system 130. Alternatively, in non-agent embodiment, rules 121 include a library of rules usable by non-agent processes. One example application of rules 121 by a rules engine includes determining actions or dispositions associated with a patient, from a number of determined conditions or recommended treatments.

Solvers library 122 includes one or more solvers, which can include non-agent solvers, agent solvers (discussed below) or both. In some embodiments, solvers, which may also be referred to as "resolvers," are applied to determine one or more conditions or recommended treatments for a patient. A finite state machine solver may be used to determine the conditions and recommended treatments of a patient suffering from a number of conditions including congestive heart failure. Solvers may also invoke or apply other solvers. Continuing this example, the finite state machine agent solver may invoke a linear solver, such as a mixed integer linear solver, to evaluate each state in order to determine the patient's condition. In one embodiment, the finite state machine returns the actual state for each clinical condition of the patient, which is then passed on to the mixed integer linear solver as parameters, to apply the mixed integer solver based on the clinical state, and content tables 124. The solvers library 122 can be updated as new solvers are available. Another example solver is the data-extraction solver, which is described in further detail below. An data-extraction solver is a type of solver that is applied to unprocessed patient information, such as a physician's narrative or patient results data, in order to generate discretized data that is usable for other solvers.

In some embodiments, agents 135, facilitate solving problems including the problems described above, by employing one or more solvers, from library of solvers 122. Furthermore, where existing rule systems may utilize forward chaining, backward chaining and combination, agents 135 can integrate these rule capabilities as well as other traditional and heuristic techniques. These agents 135, which may be referred to as agent solvers, can also leverage the best techniques for the problem at hand. They can register their abilities to the overall system and coordinate and communicate with other agents, users, or the overall system, to solve problems based on their current capabilities. Still further, new or improved solvers, which may be introduced at future times, are able to be leveraged by swapping out current agents with new agents dynamically and without the need to recompile or reconfigure the system. Thus embodiments using multi-agent system 130 can provide advantages, in some scenarios, over single-agent systems and non-agent systems. By analogy, a single celled organism is analogous to a single-agent system, while a complex multi-celled organism is analogous to the multi-agent system. Accordingly, the "reasoning" capabilities of multi-agent system 130 are superior to the "reasoning" exhibited by a single-agent system, and the multi-agent system 130 is not constrained at design time and has the ability to grow and adapt over time based on future needs not anticipated at the time of instantiation or design.

In some embodiments, agents 135 provide enhanced decision support by using multi-agent properties like collaboration, persistence, mobility and distributed-operation, autonomy, adaptability, knowledge and intelligence, reactive and proactive capability, reuse, scalability, reliability, maintainability, security, fault tolerance, trust, and other primary properties. In addition, numerous secondary properties of multi-agents in embodiments of our invention may facilitate decision support, including: reasoning, planning and learning capabilities; decentralization; conflict resolution; distributed problem solving; divide-and-conquer strategies for handling complex problems; location transparency; allowing for competing objects to be represented; goal-driven or data driven including agent to agent or user to agent; time driven; support for multiple layers of abstraction above services thereby providing flexibility, adaptability, and reuse and simplification; negotiation; hierarchies having dynamic self-organization; abilities to spawn and destroy agents as needed; utilization of transient and persistent data; abilities to address uncertain, missing or inconsistent data; sensitivity to resource and time constraints; ontology-driven functionality; flexible run-time invocation and planning; obligations; ability to act to achieve objectives on behalf of individuals and organizations; organizational influence; and other secondary properties. Examples of agents, which may be used my the multi-agent systems of embodiments of our technologies, include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: markov decision processing; approximate linear programming; natural language extraction solvers (e.g., nCode); fuzzy-neural networks, logistic and linear regression; forward chaining inference (e.g., data driven); backward chaining inference (e.g., goal driven); inductive inference; genetic algorithm; neural network including with genetic algorithm for training; stochastic; self-organizing Kohenen map; Q-learning; quasi-Newton; gradient; decision trees; lower/higher bound search; constrain satisfaction; naives bayes fuzzy; LP-solver including mixed integer multi-variable min/max solvers; Finite State Machine and HFSM; temporal difference reasoning; data mining for classification, clustering, learning and prediction; K-means; support vector machines; K-nearest neighbor classification; C5.0; apriori; EM, simulated annealing, Tabu search, multi-criteria decision making, evolutionary algorithm, and other similar solvers.

In some embodiments, where particular types of agent solvers are more efficient at handling certain patient scenarios, a planning agent may invoke the particular type of agent solver most appropriate for the scenario. For example, a finite state machine agent solver and a liner solver agent solver may be invoked by a planning agent, in a scenario involving a patient experiencing congestive heart failure.

Continuing with FIG. 1A, some embodiments of multi-agent system 130 employ decision making for applications including, for example, searching, logical inference, pattern matching and decomposition. A subset of solvers library 122 includes decision-processing solvers 123. Decision processing solvers 123 are a special set of solvers used for decision making, although it is contemplated that in some embodiments any solvers of solvers library 122 or solver agent maybe used for decision processing. Examples of agent decision procession applications include: searching, including heuristic and traditional searching; list; constraint satisfaction; heuristic informed; hill climbing; decision tree; simulated annealing; graph search; A* search; genetic algorithm; evolutionary algorithm; tabu search; logical inference; fuzzy logic; forward and backward chaining rules; multi-criteria decision making; procedural; inductive inference; pattern recognition; neural fuzzy network; speech recognition; natural language processing; decomposition; divide and conquer; goal tree and sub-goal tree; state machine; function decomposition; pattern decomposition; and other decision processing applications. In some embodiments, agents designed or instantiated with a particular decision processing application may be swapped out, in a more seamless and transparent manner than with non-agent systems, with another agent having more advanced decision processing functionality as this becomes available or is needed.

Solver content-parameters 124, which is also referred to as "content tables" 124, include parameters used for instantiating and applying the solvers. Illustrative examples of content tables 124 are provided in FIG. 6B and further described in connection to FIG. 6B. Content tables 124 provide parameters that specify information regarding conditions, drugs, contra-indications, treatments, orders or other actions, and other parameters used in conjunction with patient information to determine conditions and recommended treatments. In one embodiment, content-parameters 124 are formatted as independent tables, which might take the form of a matrix, which maybe maintained, updated, or swapped out with other tables, by health-care providers, physicians, or experts independent of patients. For example, a content table may specify parameters relating to diabetes including what factors in patient information indicate that the patient is in hypoglycemia, what factors in patient information indicate that the patient is in hyperglycemia, contra-indications, treatments such as drugs and drug dosages that should be administered, or additional testing that should be ordered. Thus in this embodiment, the content tables 124 and the patient information 110 provide the information necessary for a solver to determine patient conditions and recommended treatments. But the content tables may be updated independently, as new information, treatments, or drugs become available.

Goals 126 includes objectives which guide the system, such as embodiments of a multi-agent, single-agent, or non-agent system 130, in the selection of a plan and, ultimately, the determination what actions to take place as a result of incoming patient data. Therefore in some embodiments, goals are based on incoming patient information. For example, a goal may specify "manage conditions for heart failure," "manage conditions for heart failure and DM," "manage conditions for heart failure while keeping other patient conditions stable" or "minimize the cost of patient treatment." In some embodiments, goals are used to motivate agents 135. Specifically, agents 135 operate under guidance of a goal that is consistent with patient information, when deciding what actions to take, plans to select and execute, or which solvers to invoke. Thus any plan selected and executed will be consistent with the determined goals 126, which are based on patient information 110. Moreover, as patient information 110 changes, such as when newer or additional patient information 110 becomes available or a patient's condition changes during the course of treatment, goals 126 may be changed or replaced. In some embodiments such as multi-agent systems operating under the belief-desire-intention ("BDI") model, a goal is analogous to a desire. Accordingly, in one embodiment, agents 135 may act to fulfill a desire that is based form a set of agent beliefs or facts determined from available patient information 110. In some embodiments, goals 126 can be organized in one or more sets, groups, tables, databases, or libraries, with, in some embodiments, subgroups related to similar goal-objectives; for example, a subgroup of goals may relate to handling patient treatment costs or treating cancer.

Plans 128 includes, in some embodiments, specific executable algorithms, instructions, schedules, or the similar plans for carrying out a specific objective that is consistent with a determined goal 126. Alternatively in other embodiments, plans 128 may specify intention or an intended outcome to be achieved that are consistent with a determined goal 126. Plans 128 can include sets or libraries of plans, which in some embodiments are associated with certain goals 126. For example, for the goal of "manage conditions for heart failure while keeping other patient conditions stable" plans associated with this goal may specify actions for determining a patients condition by examining patient information including blood pressure and pulse. The plan may further specify recommended treatments, orders, or other plans to be executed. In some embodiments, plans 128 also include planning agents, which can assist in the selection and execution of a plan. For example, a planning agent may select a plan, which in some embodiments may also be an agent, for treating dystocia based on patient information that indicates dystocia; the plan may specify using logistical regression on the patient information to determine the patient's condition and recommended treatment, in one embodiment.

In another example, a specific plan under the heart failure goal described above, may specify using an data-extraction agent for extracting discrete data items from a physicians note written in natural language, and then instantiating a finite state machine solver agent to determine a patients conditions and recommended treatments. In one embodiment rather than specifying a specific solver or set of solvers to use (e.g., data-extraction and finite state machine solvers), a plan may specify an intention, (e.g., determine patients condition when patient information indicates dystocia), and invoke an agent 135 to select the best solver applicable based on the available patient information 110. Under the BDI model, a plan is analogous to an intention; thus a plan is sort of like an intention to process the goal for which the plan is associated with. The plan 128 is executed to meet the goal 126, or partially meet the goal. In one embodiment, a planning engine is used for determining plans 128 consistent with goals 126. The planning engine which could be an agent, non-agent rules engine, a decision tree, or other decision process, selects a plan.

Figure 1B:
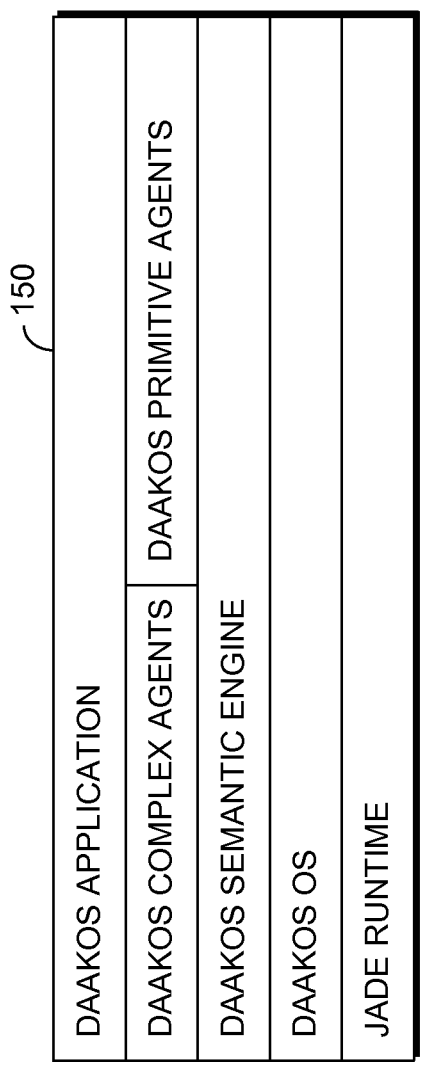
FIG. 1B depicts an exemplary framework of a multi-agent system suitable for implementing an embodiment of the invention.

Turning to FIG. 1B, an illustrative example is provided of a framework suitable for implementing a multi-agent system, such as computer system 130 of FIG. 1A, and is referenced generally by the number 150. Framework 150 has a layered architecture. At the lowest level depicted in the embodiment shown in FIG. 1B, framework 150 includes a layer for JADE runtime. In other embodiments, frameworks such as Cougaaar, Zeus, FIPA-OS, or an open-agent architecture, may be used. Although not a requirement, it is preferable that the framework include the following properties, which are present in the JADE framework: FIPA compliance; support for autonomous and proactive agents and loosely coupled agents; peer-to-peer communication; fully distributed architecture; efficient transportation of asynchronous messages; support for white and yellow page directory services; agent life-cycle management; agent mobility; subscription mechanism for agents; graphical tools for debugging and maintenance; support for ontology and content languages; library for interaction protocol; extensible kernel for extensions to build customized framework; in-process interface for launching and control; support for running agents on wireless mobile devices; integration with various web-based technologies; and pure Java implementation.

JADE, which is an acronym for Java Agent Development Framework is a middleware software development framework that is used for facilitating implementation of multi-agent systems. Specifically, the JADE platform includes functionality which facilitates the coordination of multiple agents, and functionality for facilitating the distribution of agent platforms across multiple machines, including machines running different operating systems. Moreover, JADE further includes functionality for changing system configuration at run-time by moving agents from one machine to another, as required.

Continuing with FIG. 1B, on top of the JADE runtime framework is the Distributed Adaptive Agent Knowledge operating system ("DAAKOS"). DAAKOS is a decision-support framework built upon JADE or another multi-agent framework. DAAKOS is a multi-agent framework with heuristic, adaptive, self-optimizing and learning capabilities and the ability to decompose complex problems into manageable tasks to assist clinical decision making at point of care. For example, care givers and other users can leverage this intelligent agent system to detect a change in personal health or to leverage up to date knowledge about medical conditions, preventive care, and other relevant interests. Accordingly, in one embodiment DAAKOS can be thought of as an intelligent, self-learning agent system using a cloud metaphor.

Specifically, DAAKOS utilizes multi-agents 135 that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. In some embodiments, intelligence is achieved within agents by way of support provided by a rich ontology within a semantic network. For example, a multi-level of collaborating agents 135 allows low level agents to transform data so that it can be passed on to another agent, and to continue the data transformation until the data has been completely transformed from bits of data which may sometimes represent incomplete, outdated, or uncertain data, to a form a usable collection of data with rich meaning. In this example, when it becomes necessary to attack complex problems the agent 135 is permitted to constrain and narrow its focus at an individual level to support decomposition. Domain specific agents can be leveraged in some embodiments to use an ontology to manage local domain specific resources.

The DAAKOS operating system layer handles process management, scheduling, memory, resource management, Input/Output ("I/O"), security, planning, as well as other processes traditionally handled by operating systems, and in some embodiments includes memory, which may include short, intermediate, and/or long term memory, I/O, internal agent blackboard, context switching, kernel, swapper, device resource management, system services, pager, process managers, and logging, auditing, and debugging processes. In some embodiments, the DAAKOS operating system layer is a distributed virtual operating system. On top of the DAAKOS operating system layer, in the embodiment illustratively provided in FIG. 1B, is the DAAKOS Symantec Engine, which provides the platform for DAAKOS agents 135. DAAKOS agents 135 include complex agents and primitive agents. On top of the agents layers are DAAKOS Applications. These include, for example, DAAKOS agent solvers such as a finite state machine instantiated and executed to determine a patient's conditions and recommended treatments, transactions knowledge engines, and other applications leveraging DAAKOS agents 135.

Figure 1C:
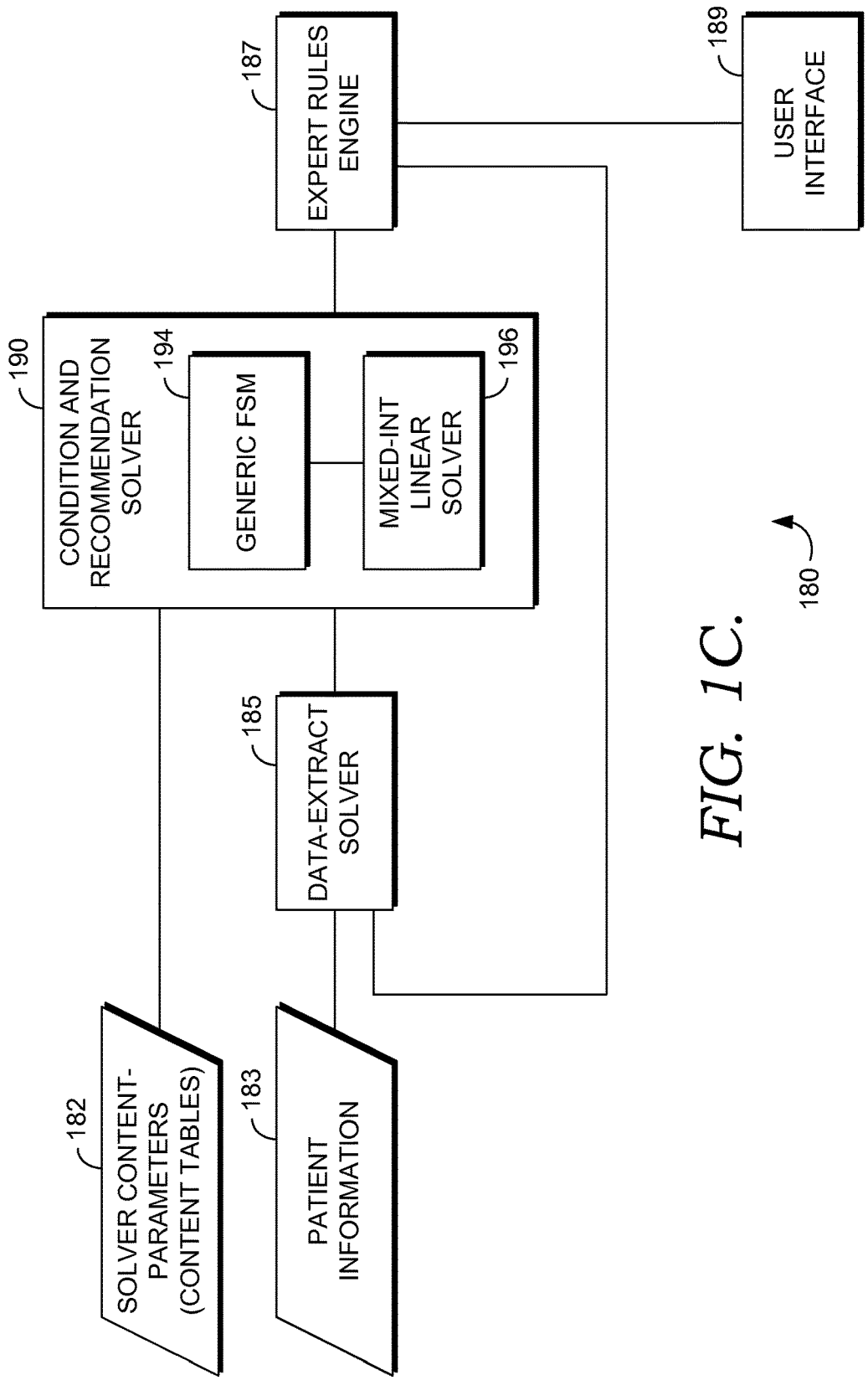
FIG. 1C depicts aspects of an illustrative operating environment suitable for practicing an embodiment of the invention.

FIG. 1C illustratively depicts a block diagram 180 showing an exemplary embodiment of the multi-agent computer system 130, patient information 110, and aspects of parameters 120 of FIG. 1A, that is suitable for determining actions and dispositions for a patient experiencing congestive heart failure. As shown in FIG. 1C, solver content-parameters 182 are communicatively coupled to condition and recommendation resolver 190. Solver content-parameters 182, also referred to as "content tables" 182, represent one or more content tables, such as content tables 124 described above in connection to FIG. 1A. In the embodiment of FIG. 1C, content tables 182 include parameters that will be used by condition and recommendation solver 190 to instantiate and apply other solvers to determine the patient's condition and recommended treatments. Patient information 183, which includes information about a patient that is described above in connection to patient information data store 110, is communicatively coupled to DAAKOS data-extraction solver 185. DAAKOS data-extraction solver 185, which in some embodiments can be an agent solver, extracts discrete patient from patient information 182. The discrete patient data is usable by other solvers or condition and recommendation resolver 195. DAAKOS data-extraction solver 185 and content tables 182 are communicatively coupled to condition and recommendation solver 190, which in one embodiment can take the form of one or more agent solvers.

Condition and recommendation solver 190 ("solver 190") receives content tables 182 and the discrete patient data provided by data-extraction solver 185 to determine a patient's condition or recommended treatments. In one embodiment, solver 190 is an agent, such as a solver agent, which may coordinate one or more solver agents to determine a patient's condition or recommended treatment. Solver 190 is communicatively coupled to expert rules engine 187. In one embodiment, expert rules engine 187 receives one or more determined conditions and recommended treatments associated with a patient and processes these to determine specific actions, results, notifications, or other orders, for that patient. For example and order may specify "aspirin every 12 hours" or "perform this test on the patient."

In one embodiment, an order may considered a trigger event, which can trigger off any rules that are written to be followed based on that trigger event. For example, some rules have an action-template may result in additional orders being issued as a result of a single order determined by expert rules engine 187, and which serves as a trigger event. The output of expert rules engine 187 can include 1) placing orders and related orders, including orders generated from rules based on a triggering event; 2) displaying patient results on user interface 189; 3) initiating actions to invoke another plan; 4) waiting for additional information input; and/or 5) other recommended actions.

In one embodiment, expert rules engine 187 is a DAAKOS expert agent, and may be data or time driven. In one embodiment, rules engine 187 takes the output of one or more solvers, such as solver 190, in whatever format it is in (e.g., percentage of risk for some condition, narratives, lists of possible treatments and their successes, of the like) and passes it off to be formatted to be usable. In one embodiment, expert rules engine 187 passes the solver output to a data-extraction solver agent, which formats the solver output into usable information by another solver or by the expert rules engine 187. In one embodiment, expert rules engine 187 is an agent solver and leverages a rules engine. The output of expert rules engine 187, in one embodiment, can be distilled for presentation by way of user-interface component 189.

User interface 189, which is communicatively coupled to expert rules engine 187, is a presentation and user interface system and is described in further detail above in connection into FIG. 1A as a display 140.

As shown in FIG. 1C, the connecting lines between various components represent communication couplings and do not necessarily imply a permanent communication connection; rather it is contemplated that in embodiments of our invention, such as multi-agent systems, components may be instantiated or accessed and communicated with as needed. Thus for example, a plan (or planning agent, in some embodiments) may specify to access patient information 183 and content parameters 182 for instantiating a finite state machine to determine a patient's condition for a patient suffering from congestive heart failure. The plan (or planning agent) may further specify accessing a data-extraction solver (which in some embodiments, can be a data-extraction solver agent), to discretize patient information 183 into usable patient data for condition and recommendation resolver 195. In other embodiments, other communicative couplings not shown in FIG. 1C may exist between components. For example, in one embodiment, the discretized patient information outputted from DAAKOS data-extraction solver 185 may be communicated to user interface 189, thereby enabling a physician to see the discretized patient information as illustratively shown for example, in FIG. 6A.

Figure 2:
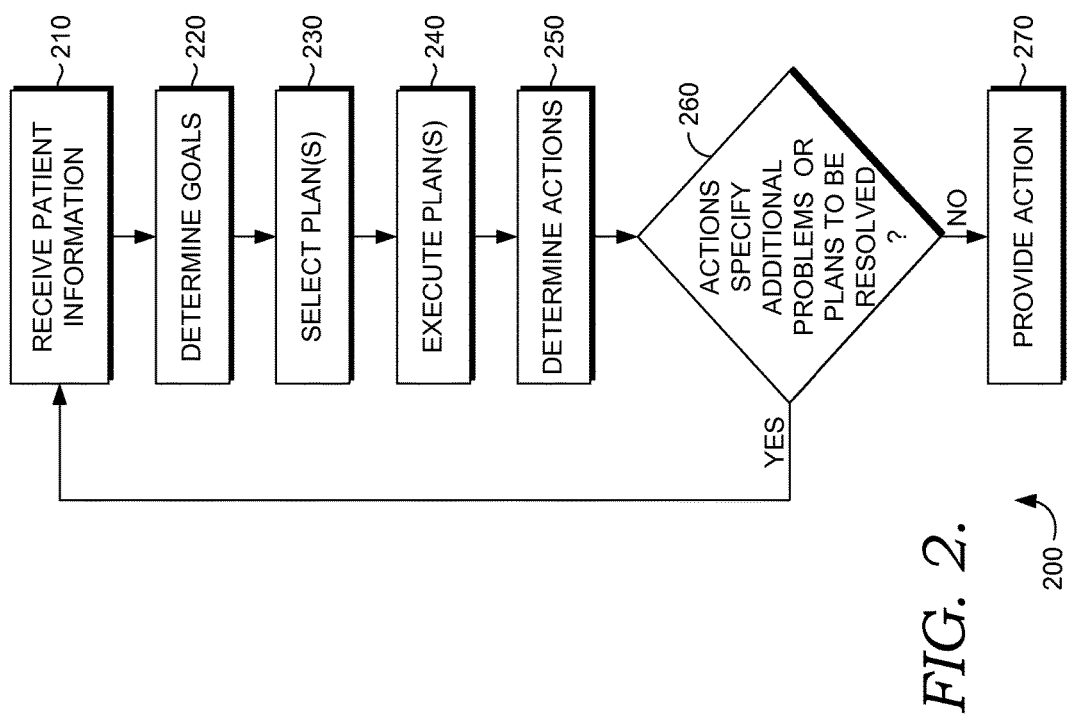
FIG. 2 depicts a flow diagram of an exemplary method for providing an action associated with a patient, in accordance with embodiments of the invention.

Turning to FIG. 2, a flow diagram 200 is provided illustrating, at a high level, an exemplary method according to one embodiment. At a step 210, patient information is received. Patient information, which is described above in connection to FIG. 1A, may be received in a variety of formats including discrete data or natural language, such as text from a physicians note. Accordingly, in some instances, it may be necessary to patient information by, for example, invoking a data-extraction solver, which may be an agent, or other parsing or extraction process to extract discrete patient information in a usable format or otherwise prepare patient information for determining goals, plans, solvers, and other processes that rely upon patient information. At a step 220, one or more goals are determined based on received patient information. For example, where patient information includes data suggesting heart failure along with other conditions, a goal relevant to heart failure may be determined, such as "manage heart failure while keeping other conditions stable." Additional details of goals are described above in connection to FIG. 1A. In one embodiment, a goal is determined by a goals agent, which considers the incoming data and selects a goal based on the data and, in one embodiment, further selects a goal that is consistent with another overarching goal, such as "save patient life" or "stabilize patient." In one embodiment, a goal may be determined from a rules engine, or decision tree, Boolean logic or similar decision process applied to received patient information.

In some embodiments, a goal is determined based on received patient information, when the received patient information indicates a trigger event. In one embodiment, a trigger event may be determined by the presence of a pattern or data or a single piece of patient information that indicates a possible likelihood of an occurrence, patient condition, patient status, or other event associated with the patient. For example, patient information relating to blood pressure and pulse may indicate that the patient is experiencing a heart attack, or may indicate, in one embodiment, that there is a 40% chance that the patient is experiencing a heart attack, based on available patient information. In one embodiment, whether a trigger event is present is determined by an agent. In another embodiment, a rules engine, a decision tree, Boolean logic, or similar solver may be applied to determine whether patient information indicates a trigger event. In one embodiment, patient information may be received continually, periodically, in intervals, or randomly, but is only acted upon when such information indicates a trigger event. Upon the detection of a trigger event, one or more goals are selected based on the trigger event.

Based on one or more goals that are determined at step 210, at a step 220, a plan is selected. In one embodiment, a plan is selected form a library of plans, such that the plan may be used to achieve the objective of the goal. Additional details of plans are discussed above in connection to FIG. 1A. In some embodiments, a single goal may have multiple plans associated with it, each plan may be executed in order or simultaneously, depending on patient information and the specific details of the plans. In some embodiments, a plan may specify the selection and execution of subsequent plans. In some embodiments, a planning agent is used to select a plan that is consistent with the determined goal, or to manage simultaneous plans. In some embodiments, a planning agent may invoke other agents to carryout specific plans. In other embodiments, a rules engine, decision tree, logic, Boolean evaluation or other decision process is used to select a plan.

By way of example of one embodiment, suppose patient information is received in real-time from EMR and HIE records for a patient with heart problems. Suppose also that patient information is received from lab results which indicate possible abnormal conditions of the patient including heart problems and other conditions. Upon entering the DAAKOS system, it is determine whether the patient information needs to be prepared for use by agents, solvers, and other system processes. If the discretized patient information does not exist, an agent may invoke a data-extraction solver agent to prepare the patient information. Once the data is prepared, it is available for other agents, processes, and components to act upon it. Properly formatted, the received patient information may indicate a trigger event—possible heart failure or a heart condition.

For example, patient information from the EMR relating to blood pressure, glucose levels, pulse, or a combination of these or other information might have abnormal values that indicate a possible heart problem. In one embodiment, logic or decision processing is applied to the patient information to determine if the information indicates a trigger event. In other embodiments, a separate plan may be invoked to manage incoming patient information events, in order to determine when patient information indicates an event.

For purposes of our example, suppose the abnormal values indicate a trigger event associated with a heart problem. Once an event is determined, a goal is determined, and based on the determined goal, a plan is selected. Here, a plan for managing heart problems might be selected, depending on the patients other conditions. The plan may be specific only to managing a heart problem, or the plan may also include processes that address the patient's other conditions. For example, if the patient is pregnant and having heart problems, the selected plan may manage the heart problem but also include actions addressing the pregnancy or alternative actions for managing the heart problem because the patient is also pregnant; for example, some tests or recommended treatments may need to be avoided.

In some embodiments, where multiple trigger events indicate are present, a planning agent or decision process, such as logic, may be employed to determine which trigger event to act on first, or which plan should be selected to address the most critical trigger events. Upon selecting the plan, in step 230, the plan is executed at a step 240.

Figure 3:
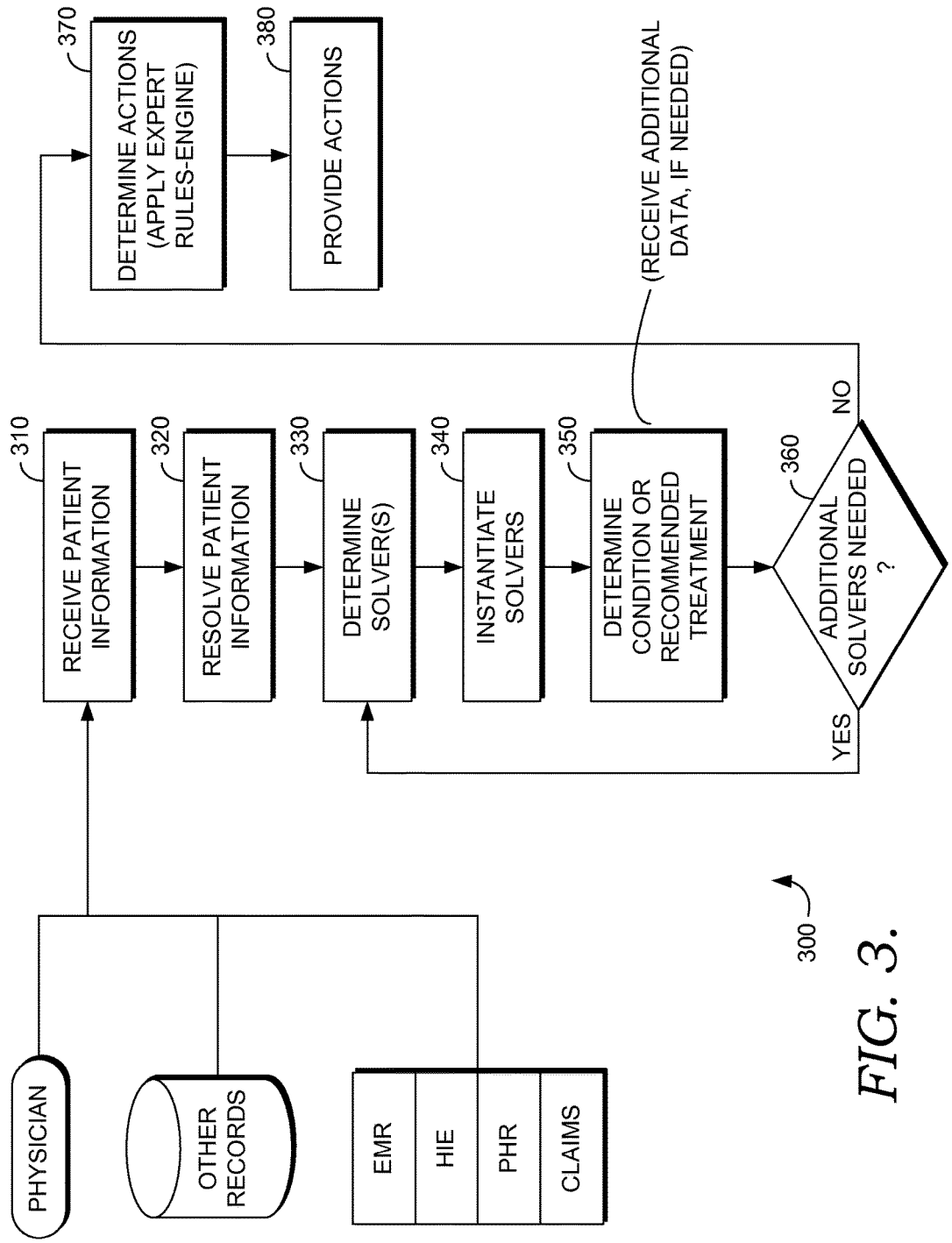
FIG. 3 depicts a flow diagram of an exemplary method for executing a plan to provide an action associated with a patient, in accordance with an embodiments of the invention.

At step 240 the selected plan is executed. A plan may specify using a particular solver or multiple solvers, content tables to be accessed for each solver, and additional patient information that is needed. FIG. 3, discussed below, provides more details of plan execution. In some embodiments, an agent, such as a planning agent, oversees selection and execution of one or more plans. In some embodiments, other agents such as solver agents can also execute plans.

In some embodiments, the output of the execution of a plan at step 240 is one or more conditions or recommended treatments associated with a patient. At a step 250, based on these conditions or recommended treatments, the specific actions, including orders, results, notifications, plans, or other actions are determined. In one embodiment, actions are determined using an expert rules engine, such the expert rules engine described in connection to FIG. 1A. In another embodiment, an agent or a non-agent decision process is used to determine one or more actions, based on the determined patient conditions and recommended treatments. In some instances a determined action may specify running another plan, performing additional testing, or based on a determined patient condition, may specify that additional problems are present. At a step 260 actions are evaluated to determine if additional problems or plans need to be resolved. If so, then the process described in FIG. 2 repeats and additional patient information is received that is relevant to the problem or plan specified by the action evaluated at step 260. For example, if at step 260 actions specify selecting and executing a second plan, then the plan may specify which patient information is needed upon returning to step 210. In some embodiments, multiple iterations of steps 210 through 260 may occur during the course of determining actions for a patient. Furthermore, in some embodiments including embodiments operating in a multi-agent system environment, some determined actions may be complete and ready to be provided at step 270, while other determined actions may specify running additional plans, and return to step 210.

At a step 270, an action is provided. As described previously and action may include orders (e.g., "aspirin every 12 hours" or "perform this test on the patient"), results, notifications, plans, or other actions associated with a patient. In one embodiment, actions are provided to a physician or other health care personnel using a user interface, such as user interface 140 described above in connection to FIG. 1A.

Turning to FIG. 3, a flow diagram 300 is provided illustrating an exemplary embodiment of a plan execution. At a step 310, patient information is received. Patient information, which is described above in connection to FIG. 1A, may be received in a variety of formats including discrete data or natural language, such as text from a physicians note. At a step 320, the patient information is resolved into information that is usable by solvers, agents, or other processes during plan execution. In one embodiment, patient information is resolved using a data-extraction solver, which may be a solver agent, or other parsing or extraction process, that extracts discrete patient information from received patient information, and formats the extracted information into a usable format, or otherwise prepares patient information for the other processes that will rely upon it. In one embodiment, resolved patient information takes the form of discretized patient results such as the example illustrative provided in FIG. 6A.

At a step 330, one or more solvers are determined. In one embodiment, the solvers are specified by the plan, which ultimately was selected based on patient information. In one embodiment, an agent, such as a planning agent determines the solvers, based on a plan or the resolved patient information, or a combination of both. In some embodiments, upon determining the solvers, one or more solver content-parameters (i.e., content table) associated with the solver, discretized patient information, or both, is accessed. The plan may specify which content tables to access, or the solver may specify this, in some embodiments. At a step 340, the one or more determined solvers are instantiated. In some embodiments, the architecture of the solvers is determined based on the content tables and the resolved patient information. For example, a finite state machine solver may have states determined by the resolved patient information and the transitions between states determined by parameters specified in a content table. An example instantiated finite state machine solver is illustratively provided in FIG. 7. In some embodiments, solvers may instantiate other solvers, as needed. For example, a finite state machine may instantiate a mixed integer linear solver for evaluating each state. In one embodiment, a finite state machine returns the actual state for each clinical condition, which is then passed on to the mixed integer linear solver as parameters, to apply the mixed integer solver based on the clinical state, and the content tables 124. In other embodiments, the plan may specify instantiating both a finite state machine solver and a linear solver for evaluating each state. In other embodiments, an agent may perform this decision.

Once solvers are instantiated, they are applied at a step 350 to determine a patient condition or recommended treatment. In some embodiments, additional data maybe needed by the solver, thus at step 350 additional patient information may be received. Again, where the patient information is not in a usable form, a data-extraction solver or other process may be employed to resolve the patient information. At a step 360, a determination is made whether additional solvers are needed. In some instances, the process started at step 350 to determine a condition or recommended treatment may require additional an additional solver. For example a finite state machine solver may require a linear solver for evaluating each state. Thus at step 260 a determination is made whether additional solvers are needed. If so, then at step 330 the additional solver types are determined, and the process repeats.

Once patient conditions and recommended treatments are determined and thus no more solvers are needed for making this determination, at a step 370 actions are determined. The actions, which can include orders, results, notifications, plans, or other actions, are determined based on the conditions or recommended treatments In one embodiment, actions are determined using an expert rules engine, such as the expert rules engine described in connection to FIG. 1A. In another embodiment, an agent or a non-agent decision process is used to determine one or more actions, based on the determined patient conditions and recommended treatments. In some instances a determined action may specify running another plan, performing additional testing, or based on a determined patient condition, may specify that additional problems are present. In these cases, the process provided in FIG. 3 may repeat, as described in FIG. 2 at step 260.

At a step 380, an action is provided. As described previously and action may include orders (e.g., "aspirin every 12 hours" or "perform this test on the patient"), results, notifications, plans, or other actions associated with a patient. In one embodiment, actions are provided to a physician or other health care personnel using a user interface, such as user interface 140 described above in connection to FIG. 1A.

Figure 4A:
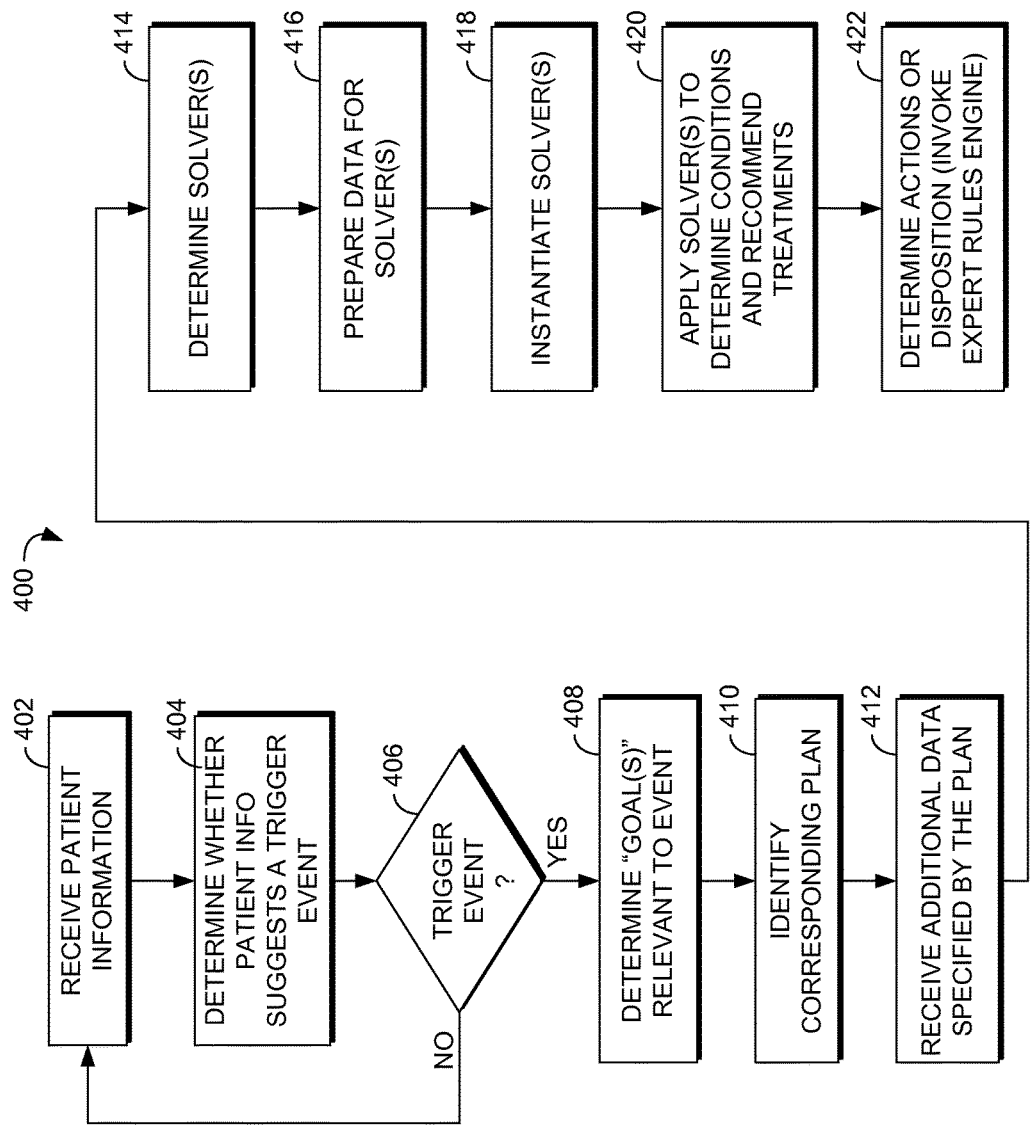
FIGS. 4A-4C depict flow diagrams of exemplary methods by which embodiments of the invention may be used to determine an action or disposition of a patient.
Figure 4C:
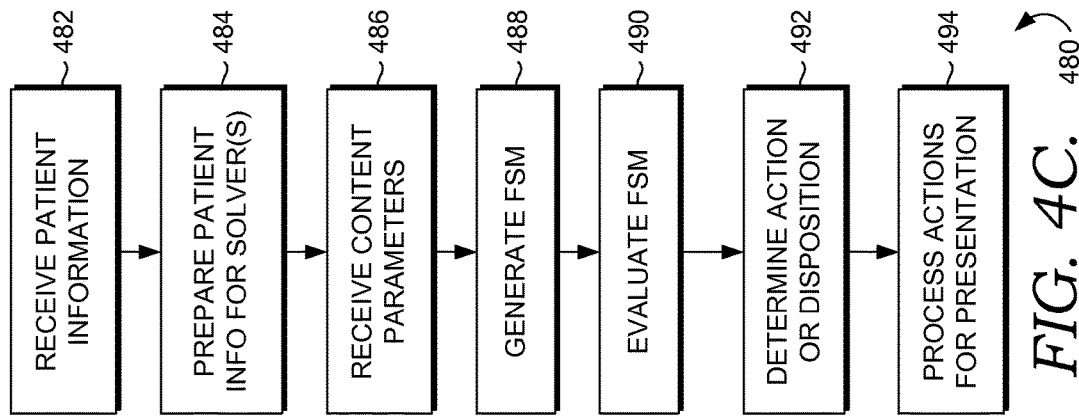
Figure 4B:
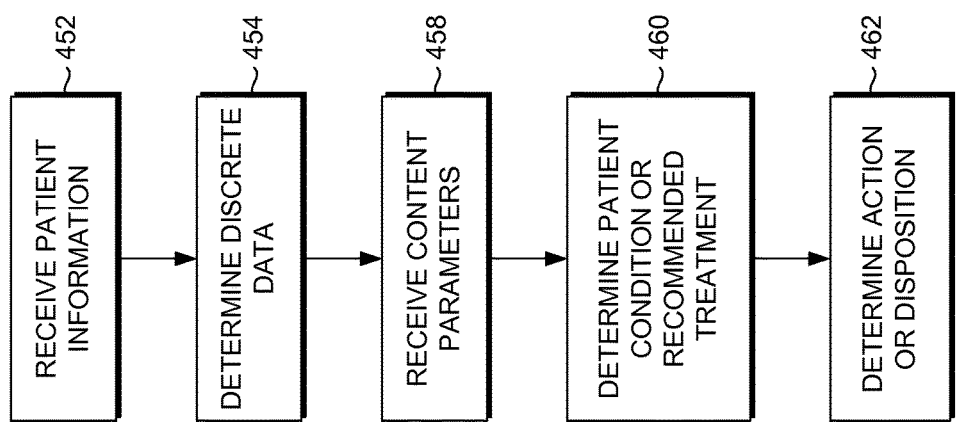

FIGS. 4A, 4B, and 4C depict flow diagrams representative of exemplary methods by which embodiments of our invention may be used to determine an action or disposition of a patient, and are shown as 400, 450, and 480, respectively. In FIG. 4A, at a step 402 patient information is received. Patient information, which is described above in connection to FIG. 1A, may be received in a variety of formats including discrete data or natural language, such as text from a physicians note. Accordingly, in some instances, it may be necessary to process patient information by, for example, invoking a data-extraction solver, which may be an agent, or other parsing or extraction process to extract discrete patient information in a usable format or otherwise prepare patient information for determining goals, plans, solvers, and other processes that rely upon patient information.

At a step 404, received patient information is processed to determine whether a trigger event is present. In one embodiment, a trigger event may be determined by the presence of a pattern or data or a single piece of patient information that indicates a possible likelihood of an occurrence, patient condition, patient status, or other event associated with the patient. For example, patient information relating to blood pressure and pulse may indicate that the patient is experiencing a heart attack, or may indicate, in one embodiment, that there is a 40% chance that the patient is experiencing a heart attack, based on available patient information. In one embodiment, whether a trigger event is present is determined by an agent. In another embodiment, a rules engine, a decision tree, logic, or other solver may be applied to patient information to determine whether patient information indicates a trigger event. In one embodiment, patient information may be received continually, periodically, in intervals, or randomly, but is only acted upon when such information indicates a trigger event.

Thus in the embodiment of FIG. 4A at step 406, if a trigger event is not indicated, then the process returns to step 402 to receive patient information. Upon the detection of a trigger event at step 406, one or more goals are selected based on the trigger event at step 408. For example, where patient information includes data suggesting heart failure along with other conditions, a goal relevant to heart failure may be determined, such as "manage heart failure while keeping other conditions stable." Additional details of goals are described above in connection to FIG. 1A. In one embodiment, a goal is determined by a goals agent, which considers the incoming data and selects a goal based on the data and, in one embodiment, further selects a goal that is consistent with another overarching goal, such as "save patient life" or "stabilize patient." In one embodiment, a goal may be determined from a rules engine, or decision tree, Boolean logic or similar decision process applied to received patient information.

Based on one or more goals that are determined at step 408, at a step 410, a plan corresponding to the determined goal or goals is selected. In one embodiment, a plan is selected form a library of plans, such that the plan may be used to achieve the objective of the goal. Additional details of plans are discussed above in connection to FIG. 1A. In some embodiments, a single goal may have multiple plans associated with it; each plan may be executed in order or simultaneously, depending on patient information and the specific details of the plans. In some embodiments, a plan may specify the selection and execution of subsequent plans. In some embodiments, a planning agent is used to select a plan that is consistent with the determined goal, or to manage simultaneous plans. In some embodiments, a planning agent may invoke other agents to carryout specific plans. In other embodiments, a rules engine, decision tree, logic, Boolean evaluation or other decision process is used to select a plan. In some embodiments, a plan will specify additional data or patient information that is needed for instantiating or applying a solver, thus at a step 412, additional patient information, content tables, or other data is received. In other embodiments, a planning agent, solver agent, other agent, or process will specify additional data to be received at step 412.

At a step 414, one or more solvers are determined. In one embodiment, the solvers are specified by the plan, which ultimately was selected based on patient information. In one embodiment, an agent, such as a planning agent determines the solvers, based on a plan or the resolved patient information, or a combination of both. In some embodiments, upon determining the solvers, one or more solver content-parameters (i.e., content table) associated with the solver, discretized patient information, or both, is accessed. The content tables may be included in the additional data received at step 412, in one embodiment. Furthermore, a plan may specify which content tables to access, or the solver may specify this, in some embodiments.

In some embodiments, additional data received at step 412, which can include additional patient information, may need to be processed into a usable format for solvers. Thus at a step 416, data, which can include patient information, is prepared for use by the solvers determined in step 414. In one embodiment, a data-extraction solver, which may be an agent, or other parsing or extraction process is employed to extract discrete patient information in a usable format or otherwise prepare patient information to be usable by the solvers.

At a step 418, the one or more determined solvers are instantiated. In some embodiments, the architecture of the solvers is determined based on the content tables and discretized patient information prepared in step 416. For example, a finite state machine solver may have states determined by the resolved patient information and the transitions between states determined by parameters specified in a content table. An example instantiated finite state machine solver is illustratively provided in FIG. 7. In some embodiments, solvers may instantiate other solvers, as needed. For example, a finite state machine may instantiate a linear solver for evaluating each state. In other embodiments, the plan may specify instantiating both a finite state machine solver and a linear solver for evaluating each state. In other embodiments, an agent may perform this decision.

Once solvers are instantiated, they are applied at a step 420 to determine a patient condition or recommended treatment. For example, in one embodiment, a finite state machine solver is evaluated. In this example, the content tables, such as example content tables illustratively provided in FIG. 6B, provide parameters specifying the transition conditions for each state of the finite state machine, while the discretized patient information, such as the illustrative example of discretized patient information provided in FIG. 6A, provides the states of the finite state machine. Accordingly, the states of the finite state machine correspond to conditions of the patient. Based on this, the finite state machine maybe traversed and the current state (i.e., condition) of the patient determined.

Figure 7:
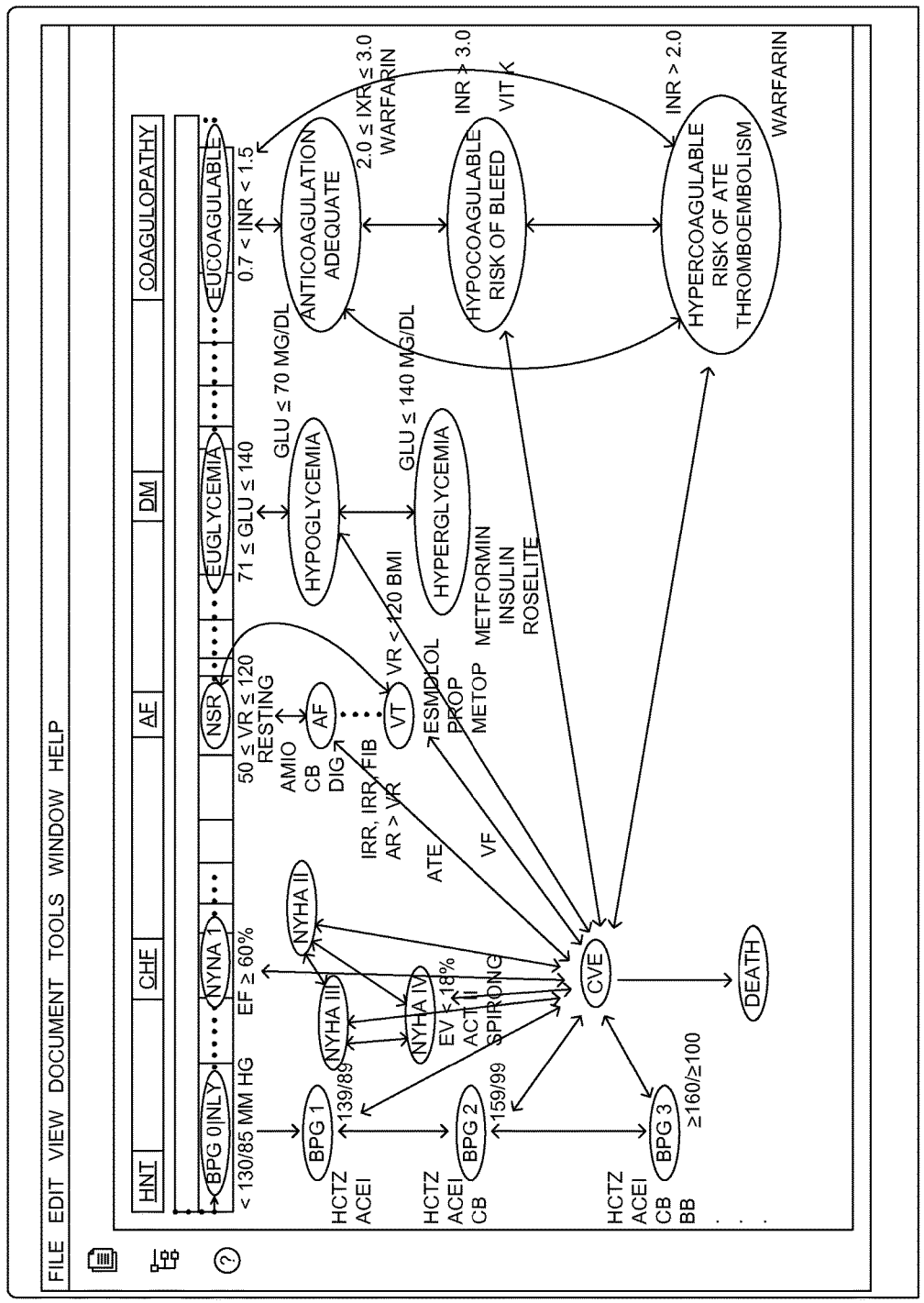
FIG. 7 depicts an illustrative example of an instantiated finite state machine solver specific to a patient and suitable for use to determine a condition or recommended treatment in an embodiment of the invention.

FIG. 7 provides an illustrative example of a finite state machine suitable for use in this example. In one embodiment, each vertical column of the finite state machine corresponds to a different condition-type of the patient, and each state within each column corresponds to a specific condition. For example, one of the columns of the finite state machine of FIG. 7 corresponds to a DM (diabetes) condition-type. Within this column, three states are present: euglycemia, hypoglycemia, and hyperglycemia. Adjacent to each state are transition parameters specifying conditions necessary to transition to another state. For example, a patient will be in the Hyperglycemia state when the discretized patient information indicates that "GLU 140 mg/dL." In some instances, evaluating each state of the finite state machine may require invoking another solver, such as a mixed integer solver—a type of linear solver. The output of step 420 is a determined condition or recommended treatment for the patient.

Once patient conditions and recommended treatments are determined, at a step 422, an action or patient disposition is determined. The action, which can include orders, results, notifications, plans, or other actions, or patient disposition is determined based on the conditions or recommended treatments. In one embodiment, this is determined using an expert rules engine, such as the expert rules engine described in connection to FIG. 1A. In another embodiment, an agent or a non-agent decision process is used to determine one or more actions, based on the determined patient conditions and recommended treatments. In some instances a determined patient disposition or action may specify running another plan, performing additional testing, or based on a determined patient condition, may specify that additional problems are present. In these cases, the process provided in FIG. 4A may repeat, as described in FIG. 2 at step 260. In some embodiments, the determined action or patient disposition may be formatted and presented to a physician, other health care personnel, or user, using a user interface, such as user interface 140 described above in connection to FIG. 1A.

Turning to FIG. 4B, at a step 452 patient information is received. Patient information, which is described above in connection to FIG. 1A, may be received in a variety of formats including discrete data or natural language, such as text from a physicians note. Accordingly, in some instances, it may be necessary to process patient information by, for example, invoking a data-extraction solver, which may be an agent, or other parsing or extraction process to extract discrete patient information in a usable format or otherwise prepare patient information for determining goals, plans, solvers, and other processes that rely upon patient information. Accordingly, at a step 454, discrete data is determined from received patient information.

At a step 458 content parameters are received. Content parameters include parameters which specify information regarding conditions, drugs, contra-indications, and other parameters used by to instantiate a particular solver, and which may be updated by physicians or experts independently of the patient. Content parameters are used by a solver to determine a patient condition or recommended treatment. In one embodiment, content parameters are content tables. In some embodiments, a plan or agent may specify which content parameters to receive. An illustrative example of content parameters is provide in FIG. 6B.

At a step 460, a patient condition or recommended treatment is determined. In some embodiments this determination is performed using one or more solvers, which can be agent solvers or non-agent decision-processes. For example, as described in connection to step 420 of FIG. 4A, a finite state machine solver may be used in conjunction with a linear solver to determine a patient condition or recommended treatments for a patient experiencing heart failure and other conditions. Once patient conditions and recommended treatments are determined, at a step 462, an action or patient disposition is determined. The action, which can include orders, results, notifications, plans, or other actions, or patient disposition is determined based on the conditions or recommended treatments determined in step 460.

In one embodiment, this is determined using an expert rules engine, such as the expert rules engine described in connection to FIG. 1A. In another embodiment, an agent or a non-agent decision process is used to determine one or more actions, based on the determined patient conditions and recommended treatments. In some instances a determined patient disposition or action may specify running another plan, performing additional testing, or based on a determined patient condition, may specify that additional problems are present. In these cases, the process provided in FIG. 4B may repeat, as described in FIG. 2 at step 260. In some embodiments, the determined action or patient disposition may be formatted and presented to a physician, other health care personnel, or user, using a user display, such as display 140 described above in connection to FIG. 1A.

Turning now to FIG. 4C, at a step 482, patient information is received. Patient information, which is described above in connection to FIG. 1A, may be received in a variety of formats including discrete data or natural language, such as text from a physicians note. Accordingly, in some instances, it may be necessary to process patient information by, for example, invoking a data-extraction solver, which may be an agent, or other parsing or extraction process to extract discrete patient information in a usable format or otherwise prepare patient information for determining goals, plans, solvers, and other processes that rely upon patient information. Accordingly, at a step 484, received patient information is prepared in a format usable by one or more solvers.

At a step 486 content parameters are received. Content parameters include parameters which specify information regarding conditions, drugs, contra-indications, and other parameters used by to instantiate a particular solver, and which may be updated by physicians or experts independently of the patient. Content parameters are used by a solver to determine a patient condition or recommended treatment. In one embodiment, content parameters are content tables. In some embodiments, a plan or agent may specify which content parameters to receive. An illustrative example of content parameters is provide in FIG. 6B.

At a step 488 a finite state machine solver is generated based on patient information prepared in step 484 and content parameters received in step 486. An example finite state machine suitable for use by the embodiment of FIG. 4C is illustratively provided in FIG. 7. In some embodiments, a plan, determined action, or other solver, will specify using a finite state machine solver. In other embodiments, an agent may specify using a finite state machine. At a step 490, the finite state machine is evaluated to determine ultimately conditions and recommended treatments of a patient. Evaluation of the finite state machine may involve invoking other solvers such as linear solver, depending on the specific patient's conditions as indicated by the prepared data of step 484 and content parameters received in step 486. The output of step 490 is one or more determined patient conditions or recommended treatments.

At a step 492, an action or patient disposition is determined. The action, which can include orders, results, notifications, plans, or other actions, or patient disposition is determined based on the conditions or recommended treatments determined through the evaluation of the finite state machine in step 490. In one embodiment, an action or patient disposition is determined using an expert rules engine, such as the expert rules engine described in connection to FIG. 1A. In another embodiment, an agent or a non-agent decision process is used to determine one or more actions, based on the determined patient conditions and recommended treatments. In some instances a determined patient disposition or action may specify running another plan, performing additional testing, or based on a determined patient condition, may specify that additional problems are present. In these cases, the process provided in FIG. 4C may repeat, as described in FIG. 2 at step 260.

At a step 494, the determined action or patient disposition is processed for presentation. In one embodiment, this is facilitated using a user interface, such as user interface 140 described above in connection to FIG. 1A. In another embodiment, an action or patient disposition is presented, via a user interface, to a physician, other health care personnel, or user. In one embodiment, the physician, other health care personnel, or user is further able to view an "explain my answer" feature which provides details regarding which plan was used, or how the plan, actions, disposition, patient condition, or recommended treatments was derived.

Figure 5:
FIG. 5 depicts an illustrative user interface showing a physicians note, determined current conditions, and recommended order sentences for a patient in accordance with embodiments of the invention.

Turning now to FIG. 5, an illustrative graphical user interface for displaying to a user is provided and referenced generally as 500. FIG. 5 shows a physicians note 510, determined current conditions 520, and recommended order sentences 530 for a patient suffering from heart failure. Physicians note 510 is shown in natural language format, such as what might be provided in narrative form from a physician. Physician's note 510 thus represents unprocessed patient information, which may be subsequently processed using a data-extraction solver or other parsing or extraction process to determine discrete patient information in a usable format or otherwise prepare patient information for determining goals, plans, solvers, and other processes that rely upon patient information. For example, FIG. 6A shows an example embodiment of discretized patient information from physician's note 510. In this example, a data-extraction solver was applied to the information of physician's note 510 to produce the discretized patient information shown in FIG. 6A.

Continuing with FIG. 5, current conditions 520 represents determined conditions or recommended treatments for a patient. Thus in one embodiment, current conditions 520 represents the output from one or more solvers using the discretized patient information, initially obtained from physician's note 510 and any content parameters necessary for instantiating and applying the solvers. Recommended order sentences 530 represents determined orders for a patient. In one embodiment, recommended order sentences 530 represents the output of a process-step to determine an action of disposition of a patient; for example in one embodiment, this may be the output of an expert rules engine, such as the expert rules engine described in connection to FIG. 1A. In another embodiment, recommended order sentences 530 represents the output of an agent or a non-agent decision process is used to determine one or more actions or patient dispositions, based on determined patient conditions and recommended treatments.

FIG. 6A depicts an illustrative example of discretized patient information, and is referenced generally by the number 600. In one embodiment, FIG. 6A represents the output of a data-extraction solver, or other parsing or extraction process, used to determine discrete patient information from received patient information that is not in an immediately usable format, such as a natural language format, for use by goals, plans, solvers, and other processes that rely upon patient information. For example, FIG. 6A shows an example of discretized patient information from physician's note 510. In this example, a data-extraction solver is applied to the information of physician's note 510 to produce the discretized patient information shown in FIG. 6A.

FIG. 6B depicts illustrative examples of solver content-parameters (i.e. content tables) suitable for use with one or more solvers to determine a condition or recommended treatment for a patient, and is referenced generally by the number 650. The content tables shown in FIG. 6B specify information regarding conditions, drugs, contra-indications, and other parameters used for instantiating a solver. Additional details regarding content tables is provided in connection to FIG. 1A, above.

In some embodiments, the parameters of the content tables determine the architecture of the solver; for example a finite state machine solver might be instantiated such that the state transitions are determined by parameters from the content tables. In some embodiments, content tables are able to be updated, generated, or replaced independently of any patient, by physicians or other experts, as new information, treatments, or drugs become available.

Turning now to FIG. 7, an illustrative example of an instantiated finite state machine solver specific to a patient suffering from heart failure and other conditions is provided and is referenced generally by the number 700. The finite state machine of FIG. 7 can be evaluated to determine the patient's specific condition and recommended treatment. In this example, content parameters, such as example content tables illustratively provided in FIG. 6B, provide parameters specifying the transition conditions for each state of the finite state machine, while the discretized patient information, such as the illustrative example of discretized patient information provided in FIG. 6A, provides the states of the finite state machine. Accordingly, the states of the finite state machine correspond to conditions of the patient. Based on this, this finite state machine maybe traversed in order to determine the current state (i.e., condition) of the patient.

In the example embodiment of FIG. 7, each vertical column of the finite state machine corresponds to a different condition-type of the patient, and each state within each column corresponds to a specific condition. For example, one of the columns of the finite state machine corresponds to a DM (diabetes) condition-type. Within this column, three states are present: euglycemia, hypoglycemia, and hyperglycemia. Adjacent to each state are transition parameters specifying conditions necessary to transition to another state. For example, a patient will be in the Hyperglycemia state when the discretized patient information indicates that "GLU 140 mg/dL." In some instances, evaluating each state of the finite state machine may require invoking another solver, such as a mixed integer solver—a type of linear solver. The output of the evaluation of the finite state machine of FIG. 7 is a determined condition or recommended treatment for the patient; an example of this is provides as current conditions 520 in FIG. 5.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized method for determining treatment for a patient having congestive heart failure and at least one other medical condition, the method comprising:
   receiving, by one or more computer processing components, patient-results information for a patient from a patient information database, wherein the patient information database is remote from at least one of the one or more computer processing components;
   extract, by the one or more computer processing components, discrete patient data from the patients-results information;
   receiving, by the one or more computer processing components, one or more rules from a parameters database, wherein the parameters database is remote from the one or more computer processing components, and wherein the one or more rules comprise a rule relevant to the discrete patient data;
   based on said discrete patient data and the one or more rules, determining, by a first processing component of the one or more computer processing components, whether said patient-results information suggests a trigger event;
   upon a determination that said trigger event has occurred, determining by a second processing component of the one or more computer processing components, at least one goal based on said trigger event, wherein the at least one goal is communicated to the one or more computer processing components by the parameters database;
   based on said goal, selecting, by the one or more computer processing components, a first plan, from a library of plans, corresponding to said determined goal, wherein the library of plans is communicated to the one or more computer processing components by the parameters database;
   in response to selecting the first plan, receiving additional patient-results information specified by said plan, wherein the additional patient-results information is communicated to the one or more computer processing components by the patient information database; and
   executing said first plan, wherein said execution comprises:
   (1) from among a library of solvers, determining a first solver to determine patient conditions and recommended treatments, said first solver comprising a finite state machine;
   (2) receiving first-solver parameters for said first solver, wherein said first solver is running on the one or more computer processing components;
   (3) preparing patient-results information for said first solver;

(4) instantiating said first solver based on said prepared patient-results information and said first-solver parameters;

(5) applying said first solver to determine said patient conditions and recommended treatments, each patient condition comprising an evaluated state for the patient condition;

(6) determining that a second solver is needed to assist said first solver to determine patient conditions and recommended treatments, wherein the second solver is running on the one or more computer processing components;

(7) invoking the second solver to assist said first solver to determine patient conditions and recommended treatments, said second solver comprising a mixed-integer linear solver, said second solver being invoked by the first solver;

(8) communicating the evaluated states for the determined said patient conditions from the first solver to the second solver;

(9) preparing patient-results information for said second solver;

(10) instantiating said second solver based on said prepared patient-results information and said evaluated states;

(11) based on said determined patient conditions and recommended treatments, communicating actions and dispositions specific to said patient from the one or more computer processing components to a second computer processing component, wherein the second computer processing component is remote from the one or more computer processing components; and

(12) displaying the communicated actions and dispositions specific to said patient on a user interface of the second computer processing component.

2. The computerized method of claim 1, wherein said actions and dispositions specific to said patient are determined by invoking an expert rules engine, and wherein said determined actions and dispositions include at least one of an order, patient condition, recommended treatment, recommended additional testing, or recommended execution of a second plan.

3. The computerized method of claim 1, wherein said determined actions and dispositions specific to said patient are processed for presentation.

4. The computerized method of claim 3, wherein said determined actions and dispositions processed for presentation further includes functionality for presenting information enabling a health-care provider to see which plan, of said library of plans, was executed and information associated with said plan including said trigger event, patient-results information, and goals.

5. The computerized method of claim 1, wherein the determination of at least one of said trigger event, goal, or plan selection are performed by a software agent.

6. The computerized method of claim 1, wherein the determination of at least one of said trigger event, goal, or plan selection are performed using logic comprising at least one of a rules engine, a Boolean evaluation, or a rules-based determination.

7. A decision support system determining treatment for a patient having congestive heart failure and at least one other medical condition, comprising:

a library of healthcare agent solvers configured for evaluating patient information to facilitate clinical decision support for the patient;

one or more computer processors; and one or more computer storage media storing computer-useable instructions that, when executed by the one or more processors, implement a method comprising:

receiving, by one or more computer processing components, patient information for the patient from a patient information database, wherein the patient information database is remote from at least one of the one or more computer processing components;

extract, by the one or more computer processing components, discrete patient data from the patients-results information;

receiving, by the one or more computer processing components, one or more rules from a parameters database, wherein the parameters database is remote from the one or more computer processing components, and wherein the one or more rules comprise a rule relevant to the discrete patient data;

based on the discrete patient data, determining, by a first processing component of the one or more computer processing components, two or more clinical conditions of the patient, at least one clinical condition including heart failure;

based on the two or more clinical conditions, determining, by the first processing component of the one or more computer processing components a set of solver-content parameters;

from a library of solvers, using the set of solver-content parameters, generating a finite state machine running on the one or more computer components having states and transition-rules corresponding to the patient information and solver-content parameters;

determining that a second solver is needed to assist said finite state machine to determine the conditions and a recommended treatment for the patient wherein the second solver is running on the one or more computer processing components;

invoking, by said finite state machine, a linear solver to assist said finite state machine to determine the conditions and the recommended treatment for the patient;

evaluating the finite state machine to determine the conditions and a recommended treatment for the patient, each state being evaluated using the linear solver, the finite state machine passing states to the linear solver;

based on the determined patient conditions and recommended treatment, communicating actions and dispositions specific to said patient from the one or more computer processing components to a second computer processing component, wherein the second computer processing component is remote from the one or more computer processing components; and displaying the communicated actions and dispositions specific to said patient on a user interface of the second computer processing component.

8. The decision support system of claim 7, wherein said action or disposition is determined by invoking an expert rules engine, and wherein said determined action or disposition includes at least one of an order, patient condition, recommended treatment, recommended additional testing.

9. The decision support system of claim 8, wherein said determined action or disposition specific to said patient are processed for presentation.

10. The decision support system of claim 7, wherein said determination of an indication of heart failure is performed by a software agent.

11. The decision support system of claim 7, wherein said determination of an indication of heart failure is performed using logic comprising at least one of a rules engine, a Boolean evaluation, or a rules-based determination.

12. A method of determining treatment for a patient having congestive heart failure, the method comprising:
  receiving, by one or more computer processing components, patient-results data, associated with a patient from a patient information database, wherein the patient information database is remote from at least one of the one or more computer processing components;
  based on said discrete patient data, determining discrete patient data operable for use by a finite state machine solver and a mixed-integer linear solver, wherein the finite state machine solver and the mixed-integer linear solver are running on the one or more computer processing components;
  determining whether said discrete patient data is indicative of heart failure;
  based on said determination of whether said patient information is indicative of heart failure, accessing heart-failure content parameters operable for use by a finite state machine solver from a memory associated with a parameters database, the parameters database being remote from the one or more computer processing components;
  based on said received content parameters and said discrete patient data, instantiating the finite state machine solver;
  determining that the mixed-integer linear solver is needed to assist said finite state machine solver to determine patient condition or recommended treatment;
  invoking, by said finite state machine solver, the mixed-integer linear solver to assist said finite state machine solver to determine patient condition or recommended treatment;
  using the finite state machine solver and the mixed-integer linear solver, determining a patient condition or recommended treatment, based on said discrete patient data and said solver-content parameters, said finite state machine solver passing states to said mixed integer linear solver;
  based on said determined patient condition or recommended treatment, applying a rules engine to determine an action; and
  initiating the action.

13. The method of claim 12, wherein said finite state machine is instantiated such that states and transition-rules for said finite state machine are determined based on said discrete patient data and said solver-content parameters, and wherein said each state of said finite state machine is evaluated using said mixed-integer linear solver.

14. The method of claim 13, wherein said determined action or disposition is processed for presentation.

15. The method of claim 12, wherein said determination of an indication of heart failure is performed by a software agent.

16. The method of claim of 12, wherein said determination of an indication of heart failure is performed using logic comprising at least one of a rules engine, a Boolean evaluation, or a rules-based determination.

17. A system for facilitating clinical decision making, comprising:
  patient information related to a patient;
  solver-content parameters operable for use to instantiate one or more solvers, from a library of solvers, for use to determine at least one condition or recommended treatment associated with said patient;
  a data-extraction solver operable to determine discrete patient data from said patient information;
  a condition and recommendation resolver agent ("resolver agent") operable to receive said discrete patient data and said solver-content parameters, and based on said discrete data and solver-content parameters, determine at least one condition or recommended treatment associated with said patient; and
  an expert rules engine operable for receiving at least one condition or recommended treatment and determining an action or disposition based on said at least one condition or recommended treatment;
  (1) said resolver agent further comprising a generic finite state machine and a mixed-integer linear solver;
  (2) said resolver agent being further operable to instantiate and execute a patient-specific finite state machine, based on said generic finite state machine, having states and transition-rules corresponding to said discrete patient data and said solver-content parameters, the patient-specific finite state machine determining that a second solver is needed to assist said first patient-specific finite state machine and invoking the mixed-integer linear solver to evaluate each state of the patient-specific finite state machine to determine the at least one condition or recommended treatment; and
  (3) said resolver agent being further operable to use said mixed integer linear solver to evaluate each state of the finite state machine.

18. The system of claim 17, wherein the generic finite state machine returns an actual state for each clinical condition of the patient, the actual states being passed to the mixed integer linear solver as parameters, to apply the mixed integer solver based on a clinical state, and content tables.

* * * * *